United States Patent
Nakayama et al.

[11] Patent Number: 5,853,705
[45] Date of Patent: Dec. 29, 1998

[54] ANTI-AGING COSMETIC COMPOSITION

[75] Inventors: Yasukazu Nakayama; Shoji Nishiyama, both of Yokohama; Yoichi Shimatani, Tokyo; Shigetoyo Sawaki, Osaka; Katsuhisa Yamada, Osaka; Kazufumi Naitoh, Osaka, all of Japan

[73] Assignee: Shiseido Company, Ltd., Tokyo, Japan

[21] Appl. No.: 823,834

[22] Filed: Mar. 25, 1997

[30] Foreign Application Priority Data

Mar. 27, 1996 [JP] Japan .................................. 8-097654

[51] Int. Cl.⁶ ....................................................... A61K 7/42
[52] U.S. Cl. .................. 424/59; 424/401; 424/94.63; 424/94.64; 424/94.65; 424/94.66
[58] Field of Search .............................. 424/401, 59, 100, 424/94.1, 94.2, 94.3, 94.6, 94.63, 94.64, 94.65, 94.66; 726/52

[56] References Cited

U.S. PATENT DOCUMENTS

| | | | |
|---|---|---|---|
| 5,204,134 | 4/1993 | Girsh | 426/580 |
| 5,560,917 | 10/1996 | Cohen et al. | 424/401 |
| 5,614,489 | 3/1997 | Mohammadi et al. | 514/2 |

FOREIGN PATENT DOCUMENTS 5-221844  8/1993  Japan .

*Primary Examiner*—Neil S. Levy
*Attorney, Agent, or Firm*—Foley & Lardner

[57] ABSTRACT

An anti-aging cosmetic composition in which is blended an enzymolyzed substance obtained by treating by one or more enzymes an alkali extract of a hypoallergenic rice obtained by treating rice in advance with a proteinase and, preferably, a UV protective agent.

19 Claims, 7 Drawing Sheets

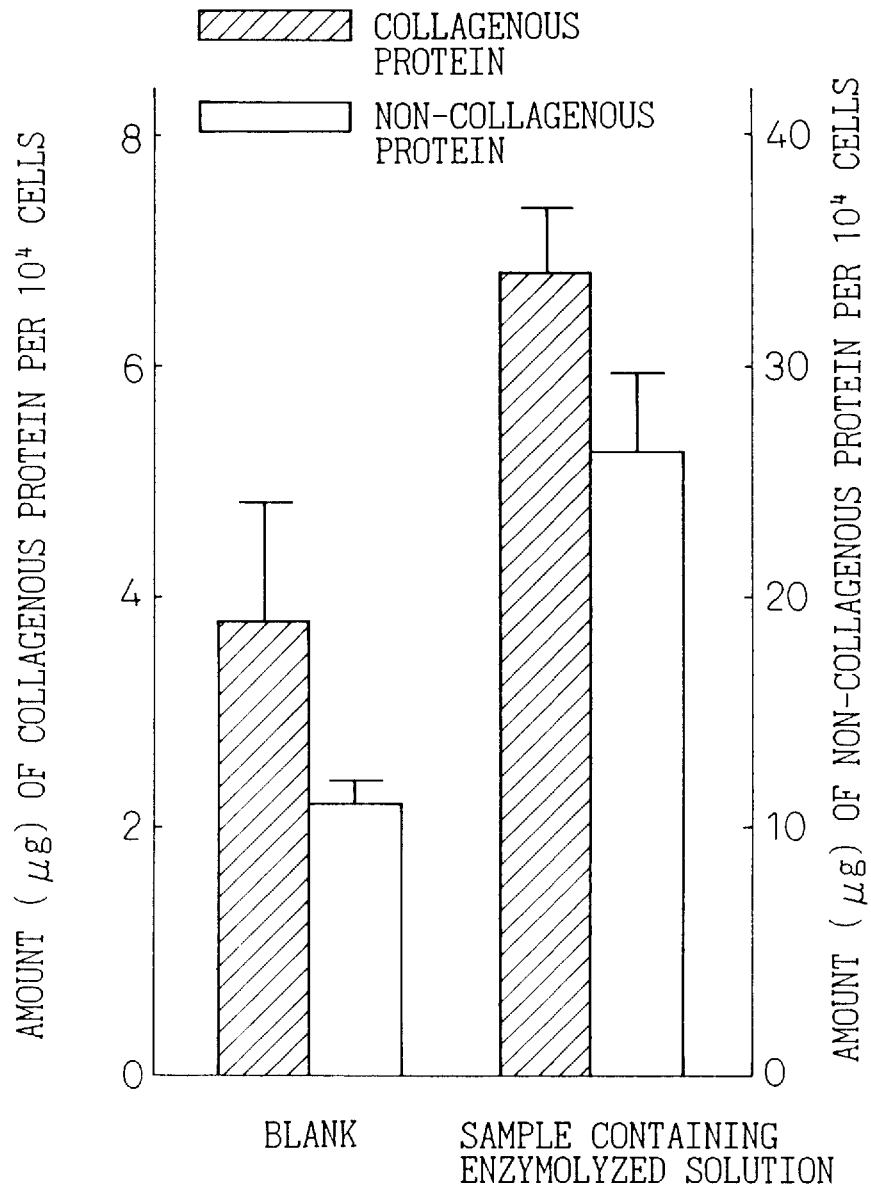

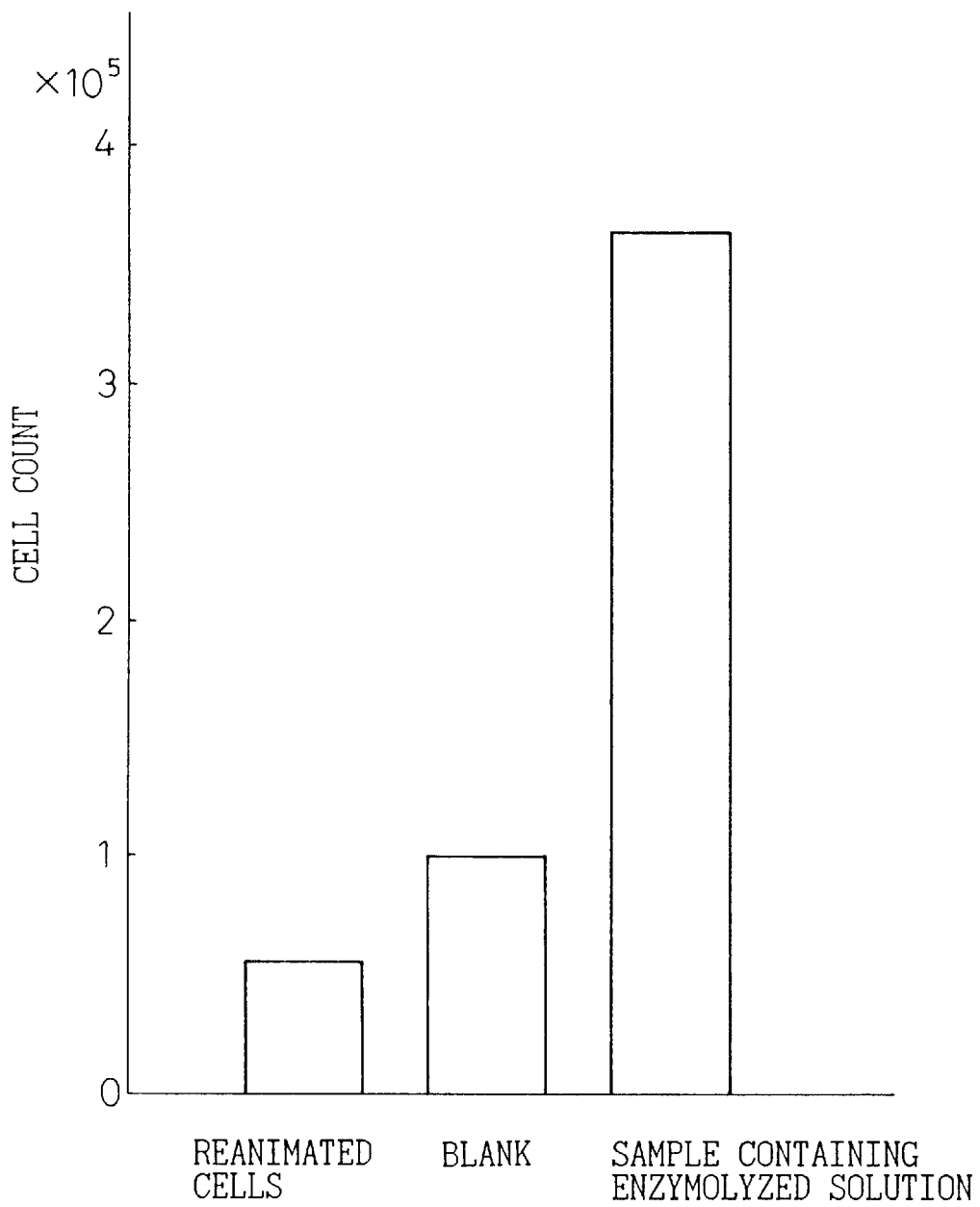

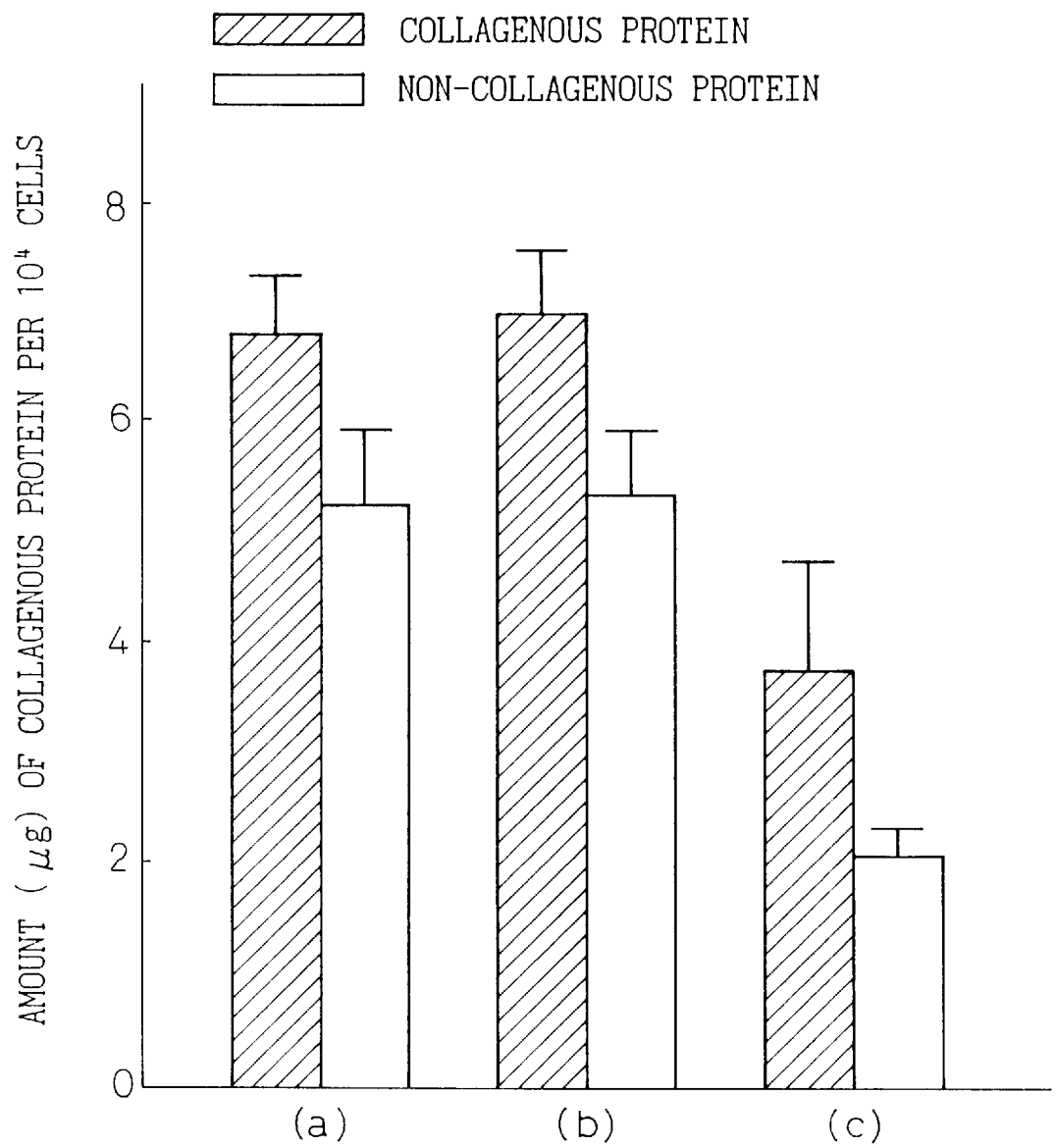

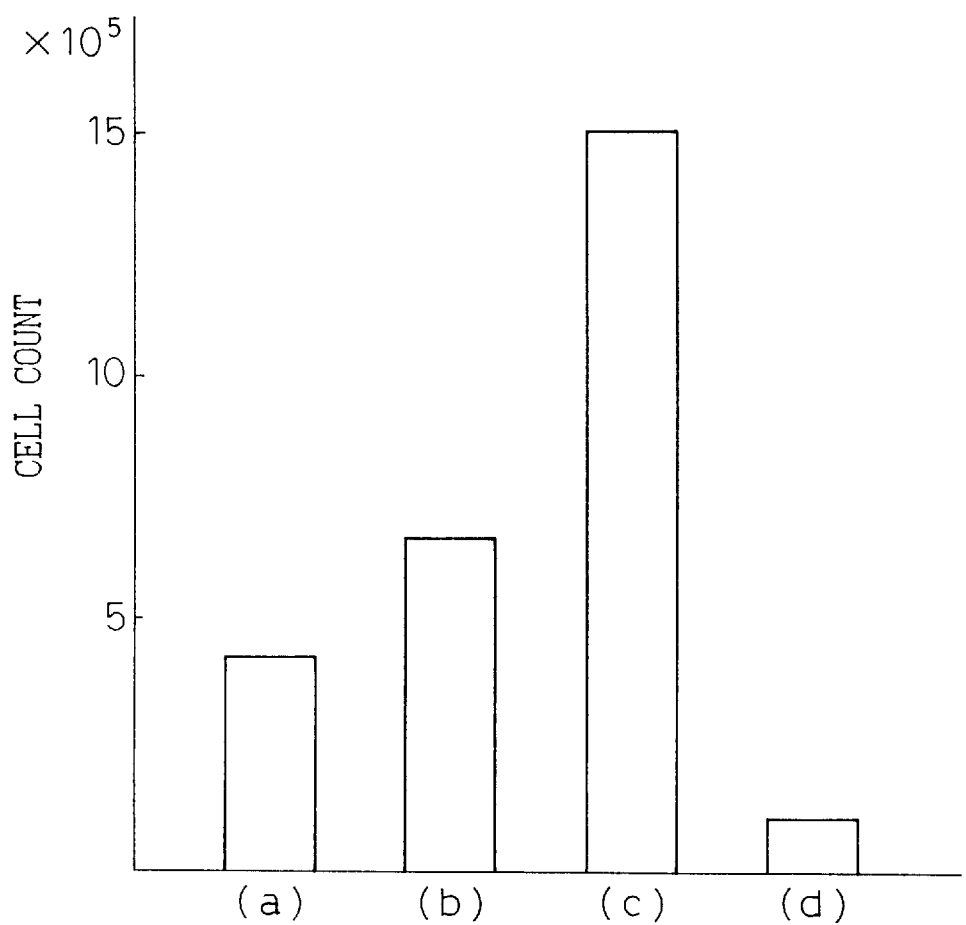

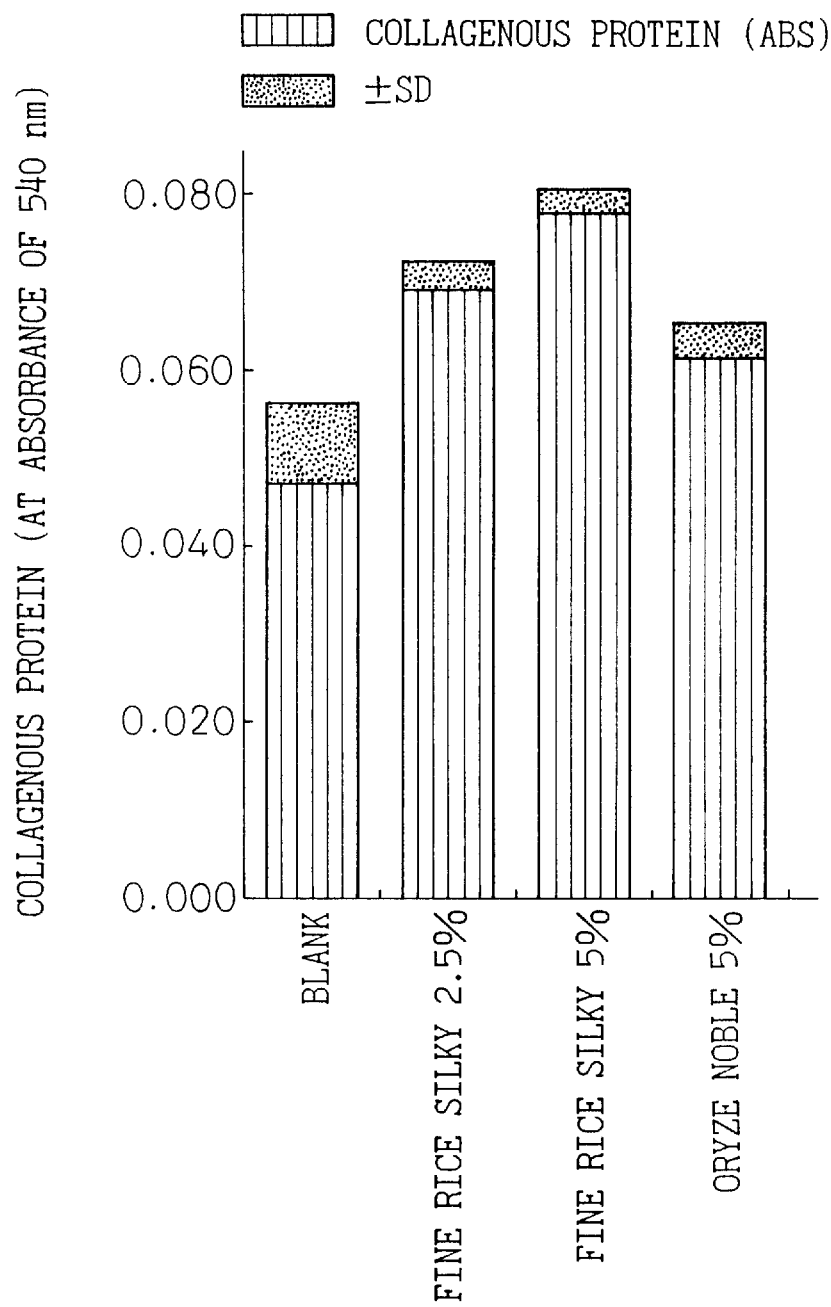

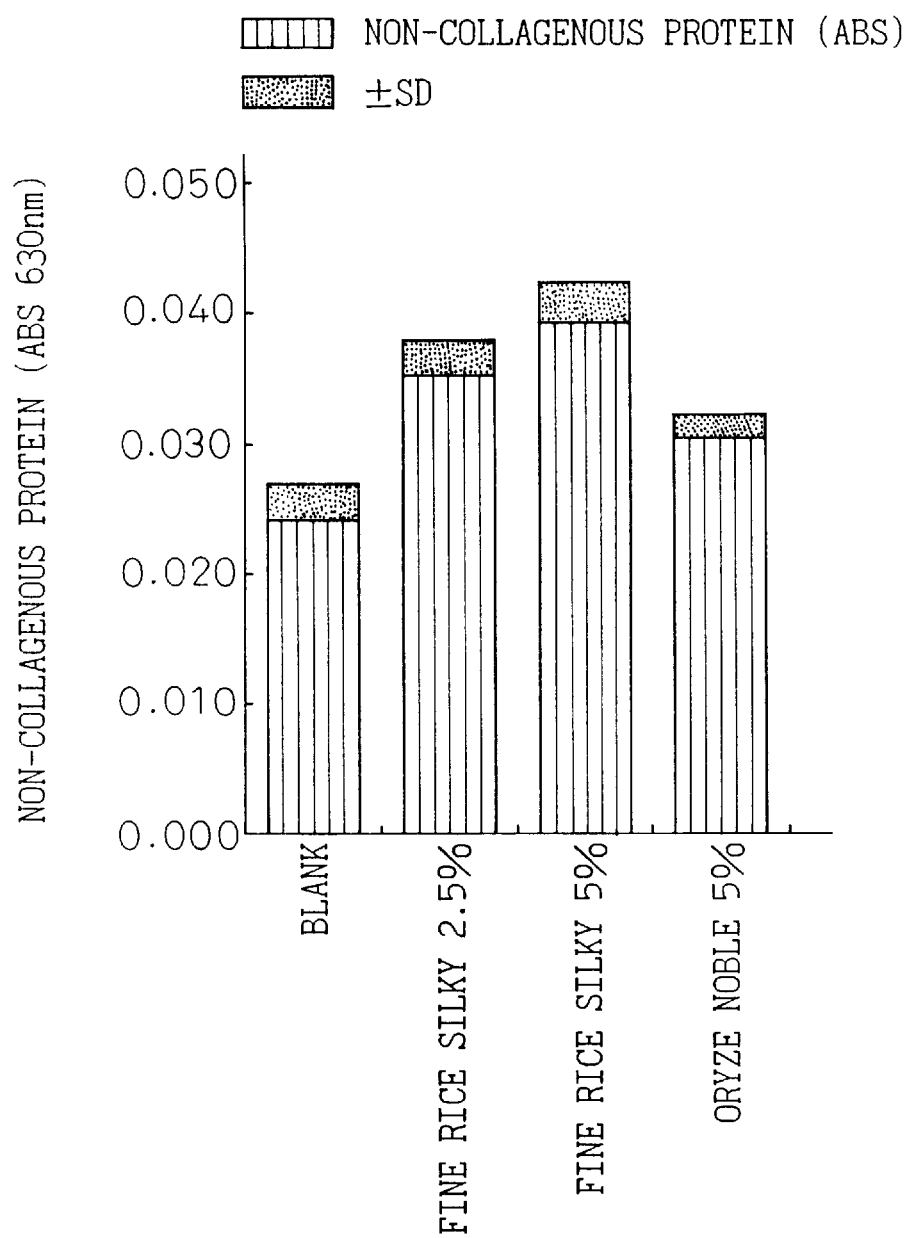

ANTI-AGING COSMETIC COMPOSITION

BACKGROUND OF THE INVENTION

1. Field of the Invention

The present invention relates to an anti-aging cosmetic composition. More specifically, it relates to a cosmetic composition exhibiting a superior anti-aging action and capable of being suitably used for basic cosmetic compositions and also makeup cosmetics, hair cosmetic compositions, bath additives, etc.

2. Descriptions of the Related Art

In the past, consideration had been given to the need for anti-aging cosmetic compositions, but since the mechanism, definition, etc. of aging had not been clear, in general it had been generally judged by measuring the state of moisture as the lushness of the skin or measuring the elasticity of the skin or by visually observing the color of the skin.

In recent years, however, there have been studies advanced on aging. As the causes for aging of the skin, viewed macroscopically, actual years has been an important factor. Further, drying, oxidation, the effects of sunlight (UV rays), etc. have been mentioned as direct factors relating to skin aging. As specific examples of skin aging, the cross-linking reaction of collagenous protein, the reduction in the hyaluronic acid and other mucopolysaccharides, cell damage by UV rays, etc. have been known, but as seen in conventional cosmetic compositions, the effort had been only to maintain moisture by blending in mucopolysaccharides or collagenous protein and other biochemical products and synthetic polymer products. With this alone, it was clear that it was not possible to sufficiently prevent aging of the skin.

SUMMARY OF THE INVENTION

Accordingly, the object of the present invention to provide an anti-aging cosmetic composition, which exhibits the superior cosmetic effect of preventing damage to the skin and allowing damage which has been received to be recovered from so as to prevent aging of the skin and maintain a young state of the skin.

In accordance with the present invention, there is provided an anti-aging cosmetic composition comprising an enzymolyzed solution obtained by treating, with at least one enzyme, an alkali extract of a hypoallergenic rice obtained by treating rice in advance with a proteinase, and one or more UV protective agents.

In accordance with the present invention, there is also provided an anti-aging cosmetic composition comprising an enzymolyzed solution obtained by treating, with at least one enzyme, an alkali extract of hypoallergenic rice obtained by treating rice in advance with a proteinase and at least one UV protective agent.

Thus, the present inventors developed a substance obtained by enzymatic treatment of hypoallergenic rice and blended this into a cosmetic composition so as to provide a cosmetic composition exhibiting the superior cosmetic effect of working on the fibroblasts in the skin and causing the production and synthesis of collagenous protein, one of the important components of the dermis, and further suppressing the peroxide lipids so as to prevent skin trouble and maintain a young state of the skin. The present invention gives a cosmetic composition which further improves on the prior art and is more superior in the anti-aging effect.

The present inventors engaged in intensive studies regarding the above problems and further found that it was possible to solve the above problems by using as effective ingredients a combination of an enzymolyzed solution obtained by treating by one or more types of enzymes an alkali extract of hypoallergenic rice obtained by treating rice in advance with a proteinase and a UV protective agent.

BRIEF DESCRIPTION OF THE DRAWINGS

The present invention will be better understood from the description set forth below with reference to the accompanying drawings, wherein:

FIG. 2 is a graph showing the amount of collagenous protein and the amount of non-collagenous protein per $10^4$ of cells in a sample containing the enzymolyzed solution obtained in Preparation Example 1 and a blank;

FIG. 3 is a graph of the number of cells in a sample containing the enzymolyzed solution obtained in Preparation Example 1 and a blank and the number of reanimated cells in the sample containing the enzymolyzed solution;

FIG. 4 is a view of the amount of collagenous protein and amount of non-collagenous protein per $10^4$ of cells in a sample (a) containing the enzymolyzed solution obtained in Preparation Example 1, a sample (b) containing the enzymolyzed solution obtained in Preparation Example 1 and 4-methoxy-4'-tert-butyldibenzoylmethane, and a blank (c);

FIG. 5 is a view of the number of cells, after irradiation by UV rays, cultured in a sample (a) containing the enzymolyzed solution obtained in Preparation Example 1, a sample (b) containing 2-hydroxy-4-methoxydibenzophenone, a sample (c) containing the enzymolyzed solution obtained in Preparation Example 1 and 2-hydroxy-4-methoxydibenzophenone, and a blank (d).

FIG. 6 is a graph showing the amount of collagenous protein per $10^4$ of cells in a sample containing the enzymolyzed solution obtained in Preparation Example 1 and Fine Rice Silky (i.e., the alkali extract of hypoallergenic rice according to the present invention); and FIG. 7 is a graph showing the amount of the non-collagenous protein per $10^4$ of cells in a sample containing the enzymolyzed solution obtained in Preparation Example 1 and Fine Rice Silky.

DESCRIPTION OF THE PREFERRED EMBODIMENT

Figure 1:
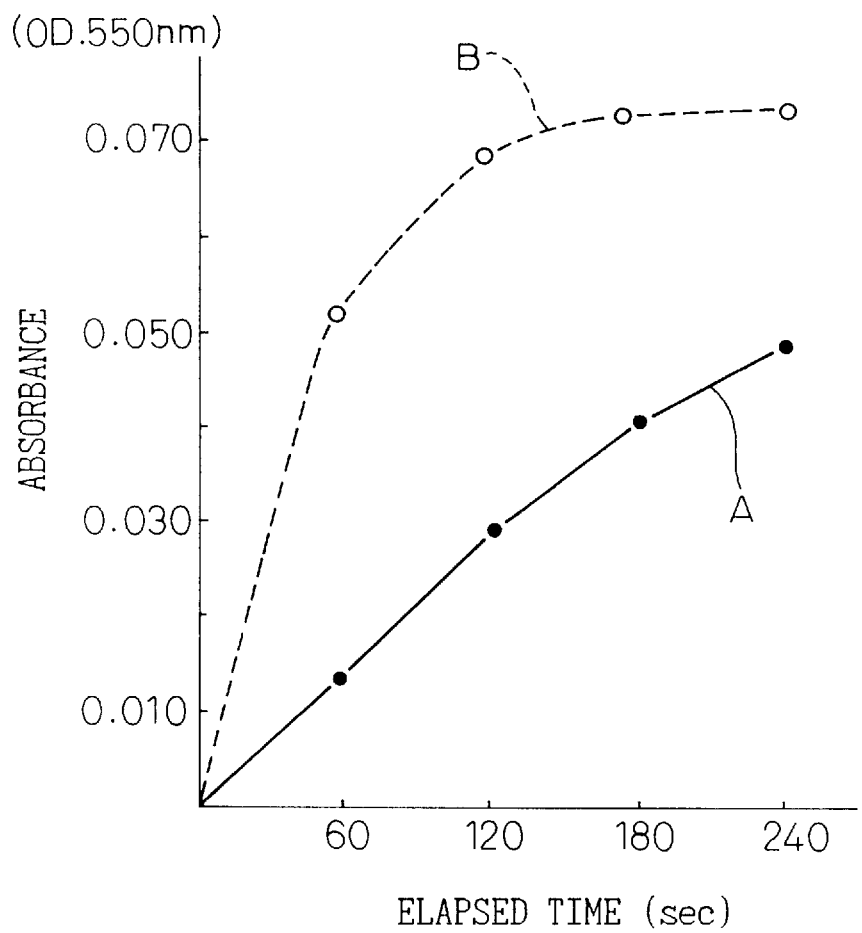
FIG. 1 is a graph showing the absorptions after the elapse of every 60 seconds at OD. 550 nm in a sample containing the enzymolyzed solution obtained in Preparation Example 1 and a blank.

The present invention will be explained in more detail below.

The hypoallergenic rice used in the present invention is obtained by treating rice with a proteinase. In the present invention, the use of this hypoallergenic rice is one of the major characterizing features. Note that the rice used is preferably usually rinsed in advance and immersed and heated in water adjusted to the optimum pH for the proteinase used.

As typical examples of the proteinase for treating the above rice, Actinase can for example be mentioned. For example, when treating rice with this Actinase, approximately 50 to 70% by weight of globulin, one of the allergens normally included in rice, which is a type of causative substance causing allergies, is decomposed and removed.

The amount of the proteinase used at the time of obtaining the hypoallergenic rice differs depending on the type of the enzyme used etc., but considering the action and effect, normally at least 0.001 part (part by weight, same below), preferably at least 0.005 part, and not more than 1 part, preferably not more than 0.1 part, is used based upon 100 parts of rice.

The time required for treatment by the proteinase differs depending on the type of the enzyme used and the decomposition temperature etc. and cannot be in general determined, but normally 1 to 48 hours or so, preferably 12 to 24 hours or so, is preferred.

Note that the decomposition temperature of Actinase illustrated above, for example, is about 30 to 40° C.

Further, in the treatment by the proteinase, the pH of the solution of the treated rice should be adjusted to give the optimum pH of the proteinase used. In adjusting the pH of the solution of the rice, when necessary, use may be made of the alkali adjusters used when performing the later explained extraction or citric acid, hydrochloric acid, phosphoric acid, sulfuric acid, or other acid adjusters.

Next, the hypoallergenic rice obtained as explained above is subjected to alkali extraction.

As the solvent used for the alkali extraction, for example, refined water or other water; ethanol or other monovalent lower alcohols; oleyl alcohol, stearyl alcohol, octyl alcohol, and other monovalent higher alcohols; ethylene glycol, propylene glycol, glycerin, 1,3-butylene glycol, and other polyols; acetone and other ketones; ethyl acetate and other esters; hexane, chloroform, benzene, and other hydrocarbon family solvents, etc. may be mentioned. These may be used alone or any mixtures thereof. Among these, from the viewpoint of the ability for use for a broad range of cosmetic applications, purified water or mixed solvents thereof with one or more of ethanol, glycerol, and 1,3-butylene glycol are preferable.

Note that when using the above mixed solvents, for example, in the case of a mixed solvent of purified water and ethanol, the ratio of volume between the two is preferably 1:1 to 25:1, in the case of a mixed solvent of purified water and glycerol, the ratio of volume between the two is preferably 1:1 to 15:1, and in the case of a mixed solvent of purified water and 1,3-butylene glycol, the ratio of volume of the two is preferably 1:1 to 15:1.

When performing the alkali extraction, an alkali adjuster such as sodium hydroxide, sodium carbonate, or other sodium salt; potassium hydroxide or other potassium salt, etc. is used so as to set the pH of the solution used for the extraction to about 7.5 to 14. Note that among these alkali adjusters, sodium hydroxide and sodium carbonate are preferred from the viewpoint of enabling adjustment to give the target pH at a low concentration.

The time required for the alkali extraction differs depending on the type of the solvent and alkali adjuster used, the desired pH, the extraction temperature, etc. and cannot be determined in general, but for example when the pH is 8.5 to 14, usually is 6 hours to 7 days or so, preferably 24 hours to 48 hours or so. Note that the extraction temperature is desirably 4° to 40° C. or so, preferably 4° to 20° C. or so.

Next, the alkali extract obtained as explained above is treated with one or more enzymes.

As the above enzymes, for example, Actinase and other Actinases, pepsin and other pepsins, trypsin, chymotrypsin, and other trypsins, papain, chemopapain, and other papains, glycylglycine peptidase, carboxypeptidase, aminopeptidase, and other peptidases, bromelin and other proteinases, etc. may be mentioned. Among these, one or more types may be selected for use. Among these, Actinase and a combination of at least one proteinase selected from pepsins, trypsins, papains, peptidases, and bromelin are preferred from the viewpoint of the further superiority in storage stability and safety of the anti-aging cosmetic composition in which the obtained enzymolzed solution is blended. Actinase and a combination of pepsin and trypsin are particularly preferred.

Note that when treating with two or more enzymes, usually one type is used at a time.

The amount of use of the enzyme per time during the enzymatic processing differs also depending on the type of the enzyme used, but considering the action and effect, at least 0.0005 part, preferably at least 0.001 part, and not more than 0.05 part, preferably not more than 0.005 part, for a total of 0.003 to 0.015 part or so, per 100 parts of the alkali extract is desirable.

The time required for the enzymatic treatment differs depending on the type of the enzyme used and the decomposition temperature etc. and cannot be determined in general, but is normally 1 to 24 hours or so per type of the enzyme, preferably 2 to 4 hours or so. Note that the decomposition temperature of the enzymes illustrated is about 30° to 50° C.

The enzymolyzed solution obtained in this way includes normally 2% by weight or so of solid component. This enzymolyzed solution may be blended into an anti-aging cosmetic composition as it is, for example, may be blended in after concentration under reduced pressure and adjustment of the concentration, or, for example, may be blended in after being powderized by the freeze drying method or spray drying method.

Note that the enzymolyzed solution obtained is preferably adjusted to a pH of 4 to 8 from the viewpoint of the safety to the skin.

The amount of the enzymolyzed solution blended into the anti-aging cosmetic composition differs depending on the type of the desired cosmetic composition and cannot be determined in general, but to sufficiently manifest the anti-aging action by the blending of the enzymolyzed solution, at least 0.00001 part, preferably at least 0.0001 part, per 100 parts of the anti-aging cosmetic composition is desirable. Further, for stably blending it in the cosmetic composition, not more than 10.0 parts, preferably not more than 2.0 parts, converted to solid content, per 100 parts of the anti-aging cosmetic composition is preferable.

The enzymolyzed solution used in the present invention simultaneously exhibits a superior action of suppressing the production of peroxide lipids on the human skin, an activating action like superoxide disumtase (hereinafter referred to as "SOD"), an action promoting the synthesis of collagenous protein, and an action restoring UV damage, so the anti-aging cosmetic composition in which the enzymolyzed solution is blended can prevent aging of the skin and maintain a youngish healthy state of the skin. Further, since the enzymolyzed solution is prepared from hypoallergenic rice obtained with treating rice in advance with a proteinase, the enzymolyzed solution of course has a low allergenicity and can prevent the precipitation of insolubles over time, so the stability of the quality is high and the storage stability is extremely superior.

The anti-aging cosmetic composition of the present invention may further have blended in it a UV protective agent.

Here, a "UV protective agent" is a concept including both of a "UV absorber", that is, a substance which absorbs UV rays chemically, and a "UV scattering agent", that is, a substance which scatters and reflects the UV rays by a physical action.

By blending into the anti-aging cosmetic composition of the present invention a UV protective agent, it is possible to synergistically manifest the desired effects in the anti-aging cosmetic composition of the present invention.

In the anti-aging cosmetic composition of the present invention, the amount of the UV rays reaching the skin, which has an extremely deep involvement in the activity of fibroblasts and collagenous protein crosslinking, is reduced and the effect of the enzymolyzed rice easily manifests itself so the elasticity of the skin is held more and it becomes possible to prevent wrinkles or sagging and as a result it is possible to obtain an anti-aging cosmetic composition which can maintain beautiful skin more effectively.

That is, by blending into the anti-aging cosmetic composition of the present invention as effective ingredients a UV protective agent and an enzymolyzed solution obtained by treating with one or more types of enzymes an alkali extract of hypoallergenic rice obtained by treating rice in advance with a proteinase, the serious actions promoted by exposure to UV rays such as the reduction in the activity of fibroblasts and crosslinking of collagenous protein are suppressed and it is possible to obtain an anti-aging cosmetic which exhibits more superior anti-aging effects than even an anti-aging cosmetic composition in which the above enzymolyzed solution is blended as the sole effective ingredient.

In the present invention, the types of the UV scattering agent able to be provided are not particularly limited so long as they can be blended into the cosmetic composition of the present invention physicochemically and can exhibit the above synergistic effect. Accordingly, while UV protective agents are listed below, it goes without saying that the UV protective agents which can be blended into the anti-aging cosmetic composition of the present invention are not limited to these UV protective agents.

That is, as the long wavelength UV ray (UVA) absorbers, methyl anthranilate, homomentyl-N-acetylanthranilate, and other anthranilate family UV absorbers; 2,4-dihydroxybenzophenone, 2,2-dihydroxy-4-methoxybenzophenone, 2,2'-dihydroxy-4,4'-dimethoxybenzophenone, 2,2,4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid, 4-phenylbenzophenone, 2-ethylhexyl-4'-phenyl-benzophenone-2-carboxylate, 2-hydroxy-4-n-octoxybenzophenon, 4-hydroxy-3-carboxybenzophenone, and other benzophenone family UV absorbers; 2,2'-hydroxy-5-methylphenylbenzotriazole, 2-(2'-hydroxy-5'-t-octylphenyl)benzotriazole, 2-(2'-hydroxy-5'-methylphenyl) benzotriazole, and other benzotriazole family UV absorbers; dianisoylmethane, 4-methoxy-4'-t-butyldibenzoylmethane, etc. may be exemplified.

Among these long wavelength UV absorbers, 4-methoxy-4'-tert-butyldibenzoylmethane, 2-hydroxy-4-methoxybenzophenone, and 2-hydroxy-4-methoxybenzophenone derivatives, for example, 2-hydroxy-4-methoxybenzophenone-5-sulfonates are long wavelength UV absorbers superior in safety and effectiveness.

Further, as medium wavelength UV (UVB) absorbers, para-aminobenzoic acid (hereinafter referred to as "PABA"), PABA monoglycerin ester, N,N-dipropoxy-PABA-ethyl ester, N,N-diethoxy-PABA ethyl ester, N,N-dimethyl-PABA-ethyl ester, N,N-dimethyl-PABA-butyl ester, N,N-dimethyl-PABA-amyl ester, and other benzoate family UV absorbers; dipropylene glycol salicylate, ethyl-ene glycol salicylate, myristyl salicylate, methyl salicylate, amyl salicylate, menthyl salicylate, homomenthyl salicylate, octyl salicylate, phenyl salicylate, benzyl salicylate, p-isopropanolphenyl salicylate, and other salicylate family UV absorbers; octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glycerylmono-2-ethylhexanoyl-diparamethoxy cinnamate, octyl methoxycinnamate, 3,4,5-trimethoxycinnamate-3-methyl-4-[methylbis(trimethylsiloxy)silyl]butyl, p-dimethoxycinnamate monoethyl esters, and other cinnamate family UV absorbers; 3-(4'-methylbenzylidene)-d,1-camphor, 3-benzylidene-d,1-camphor, 5-(3,3-dimethyl-2-norbornylidene)-3-penten-2-one and other camphor derivatives; urocanic acid, urocanate ethyl esters, 2-phenyl-5-methylbenzoxazole, dibenzalazine, etc. may be exemplified.

Further, as the UV scattering agents, titanium oxide ($TiO_2$), talc ($MgSiO_2$), carmine ($FeO_2$), bentonite, kaolin, zinc oxide (ZnO), etc. may be mentioned.

These UV protective agents may be blended suitably combined in accordance with the specific objective and form of the anti-aging cosmetic composition of the present invention prepared.

It is known that the reduction of the activity of fibroblasts and the collagenous protein crosslinking are phenomena in the dermis of the skin. Accordingly, when blending a UV protective agent in the anti-aging cosmetic composition of the present invention, it is preferable to positively blend in a long wavelength UV (UVA: 320 to 400 nm) absorber able to easily reach the dermis rather than a medium wavelength UV (UVB: 280 to 320 nm) absorber.

Note that the medium wavelength UV absorber and long wavelength UV absorber here do not necessarily mean ones which can absorb only the medium wavelength UV rays or long wavelength UV rays, but mean ones which can absorb at least the UV rays of these wavelengths. For example, the benzophenone family UV absorbers mentioned above as long wavelength UV (UVA: 320 to 400 nm) absorbers can also absorb medium wavelength UV rays of course.

The amount of the UV protective agent blended in can be suitably changed based upon the properties to be imparted to the anti-aging cosmetic composition of the present invention, but usually it is at least 0.01% by weight and not more than 30.0% by weight, preferably at least 0.1% by weight and not more than 20.0% by weight, with respect to the entire anti-aging cosmetic composition. If the amount blended is less than 0.01% by weight of the anti-aging cosmetic composition of the present invention as a whole, there is a tendency for the synergistic effect obtained by blending in the UV protective agent not to be sufficiently manifested. Further, even when blended in over 30.0% by weight of the entire anti-aging cosmetic composition, there is a tendency for no reinforcement to be seen in the synergistic effect commensurate with the increase in the amount blended.

The anti-aging cosmetic composition of the present invention containing the effective ingredients listed above can sufficient exhibit the desired effect of promoting the synthesis of collagenous protein, suppressing the production of peroxide lipids, an SOD-like activating action, elimination of the harmful effects of UV exposure, and suppression of aging of the skin, but blending into the anti-aging cosmetic composition of the present invention the following medicinal ingredients is possible to the extent where that blending does not impair the desired effect of the present invention.

For example, giving a moisturizing effect is useful for the purpose of preventing aging of the skin due to drying. In this case, for example, polyethylene glycol, propylene glycol, glycerol, 1,3-butylene glycol, hexylene glycol, xylitol, sorbitol, maltitol, chondroitin sulfuric acid, hyalonic acid, mucoitin sulfuric acid, carbonic acid, atelocollagenous protein, cholesteryl-12-hydroxystearate, sodium lactate, gallates, dl-pyrrolidone carboxylates, short chain soluble collagenous protein, diglycerin (EO) PO adducts, IZAYOI-BARA extract, yarrow extract, Sweet Clover Extract, and other moisturizers may be blended into the anti-aging cosmetic composition of the present invention.

Giving a whitening effect is useful for the purpose of easing the harmful effects of UV rays on the skin. In this case, placenta extract, glutathione, saxifrage extract, and other whiteners may be blended into the anti-aging cosmetic composition of the present invention.

Giving an antiphlogistic effect is useful for the purpose of easing the harmful effects of UV rays on the skin in the same way as above. In this case, a glycyrrhizic acid derivative, glycyrrhetic acid derivative, salicylic acid derivative, hinokitiol, zinc oxide, allantoin, and other antiphlogistic agents may be blended into the anti-aging cosmetic of the present invention.

Similarly, for the purpose of easing the harmful effects of UV rays on the skin and suppressing aging of the skin etc., royal jelly, photosensitive agents, cholesterol derivatives, fetal calf serum extract, and other activating agents; nonylate valenyl amide, nicotinate benzyl esters, nicotinate β-butoxyethyl esters, capsaicine, zingerone, cantharis tincture, ichthammol, caffeine, tannic acid, α-borneol, tocopherol nicotinate, inositol hexanicotinate, cyclandelate, cinnarizine, trazoline, acetylcholine, verapaml, cepharanthine, γ-oryzanol, and other blood circulation promoters; sulfur, thianthol, and other antiseborrheics, etc. may be blended into the anti-aging cosmetic composition of the present invention.

Further, for various purposes, an Pheilodendron Bark Extract, goldthread extract, lithospermum extract, peony extract, swertia extract, birch extract, sage extract, loquat extract, ginseng extract, aloe extract, mallow extract, iris extract, grape extract, coicus semen extract, dishcloth gourd extract, lily extract, saffran extract, Chidium Rhiozome Extract, Ginger Extract, hypericum extract, Restharrow Extract, rosemary extract, garlic extract, cayenne extract, dried orange peel, Japanese Angelica Root Extract, and other plant extracts may be blended into the anti-aging cosmetic composition of the present invention.

Further, to give the inherent effects of various vitamins, for example, the effect of suppression of aging of the skin, to the anti-aging cosmetic composition of the present invention, vitamin A oil, retinol, retinol acetate, retinol palmitate and other vitamin A's, riboflavin, riboflavin butyrate, flavinadenine nucleotide, and other vitamin $B_2$'s, pyridoxine hydrochlorates, pyridoxine dioctanoates, and other vitamin $B_6$'s, L-ascorbic acid, L-ascorbate dipalmitate esters, sodium L-ascorbate-2-sulfate, L-ascorbate phosphate esters, dipotassium DL-α-tocopherol-L-ascorbate phosphate diester, L-ascorbate monopalmitate ester, L-ascorbate stearate ester, L-ascorbate-2-glycoside and other vitamin C's, calcium pantothenate, D-pantothenyl alcohol, pantothenyl ethyl ether, acetyl pantothenyl ethyl ether, and other pantothenic acids, ergocalciferol, cholecalciferol, and other vitamin D's, nicotinic acid, nicotinic acid amide, benzyl nicotinate, and other nicotinic acids, α-tocopherol, tocopherol acetate, DL-α-tocopherol nicotinate, DL-α-tocopherol succinate, and other vitamin E's, vitamin P, biotin, and other vitamins may be blended into the anti-aging cosmetic composition of the present invention.

Note that the medicinal components able to be blended into the anti-aging cosmetic composition of the present invention are not limited to the above mentioned medicinal components. Further, the medicinal effects corresponding to the medicinal components mentioned above are not limited to the above. For example, vitamin C's may be used as whitening components and may be used as anti-oxidation adjuvants as well. Further, the medicinal components mentioned above may be blended into the anti-aging cosmetic composition of the present invention alone or two or more of the above medicinal components may be blended in suitable combinations according to purpose.

The present invention can be applied to a wide range of cosmetic compositions, quasidrugs, etc. used for the external skin. It may take a broad range of forms such as aqueous solutions, dissolvable systems, emulsions, powders, oils, gels, ointments, aerosols, water-oil two-phase systems, water-oil-powder three-phase systems, etc. That is, if basic cosmetic compositions, it may be applied in the above various forms for facial cleansers, toilet water, emulsions, creams, gels, essences (beauty lotions), packs, masks, and other types of cosmetics. Further, if a makeup cosmetic composition, it may be used for a wide range of types of cosmetics composition such as foundations while if a toiletry product it may be used for body soap, facial soap, etc. Further, if a quasidrug, it can be used for a wide range of applications such as various ointments. Further, the types able to be assumed by the anti-aging cosmetic of the present invention are not limited to these forms and types.

Further, the anti-aging cosmetic composition of the present invention acts on the area around the hair roots and the hair and is effective in preventing split ends and broken hairs and protecting the hair, so for example can be used also as a shampoo, rinse, treatment, conditioner, hair lotion, or other hair product.

In the anti-aging cosmetic composition of the present invention, it is possible to blend in a broad range of the usual known substrates based upon the above desired form and type to an extent where this blending does not impair the desired effect of the present invention.

That is, as a liquid oil, avocado oil, tsubaki oil, primrose oil, turtle oil, macademia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, teaseed oil, kaya oil, rice bran oil, China wood oil, Japanese wood oil, jojoba oil, germ oil, triglycerin, glycerin trioctanate, glycerin triisopalmitate, etc., as the solid oils and fats, cacao butter, coconut oil, horse fat, hardened coconut oil, palm oil, beef tallow, sheep fat, hardened beef tallow, palm kernal oil, hog fat, beef bone fat, Japan wax nut oil, hardened oil, beef hoof fat, Japan wax, hardened castor oil, etc., as the waxes, beeswax, candelilla wax, cotton wax, carnauba wax, bayberry wax, insect wax, spermaceti, montan wax, rice bran wax, lanolin, kapok wax, lanolin acetate, liquid lanolin, sugarcane wax, isopropyl lanolin fatty acid, hexyl laurate, hydrogenated lanolin, jojoba wax, hard lanolin, shellac wax, POE lanolin alcohol ether, POE lanolin alcohol acetate, POE cholesterol ether, polyethylene glycol lanolin fatty acid, POE hydrated lanolin alcohol ether, etc., and as the hydrocarbon oils, liquid paraffin, ozokerite, squalane, pristane, paraffin, ceresine, squalene, vaseline, microcrystalline wax, and other oils may be mentioned.

As a higher fatty acid, for example, lauric acid, myristic acid, palmitic acid, stearic acid, behenic acid, oleic acid, 12-hydroxystearic acid, undecylic acid, toluic acid, isostearic acid, linolic acid, linoleic acid, eicosapentaenoic acid (EPA), docosahexaenoic acid (DHA), etc. may be mentioned.

As a higher alcohol, for example, lauryl alcohol, cetyl alcohol, stearyl alcohol, behenyl alcohol, myristyl alcohol, oleyl alcohol, cetostearyl alcohol, and other straight chain alcohols, monostearyl glycerin ether (batyl alcohol), 2-decyltetradecinol, lanolin alcohol, cholesterol, phytosterol, hexyldodecanol, isostearyl alcohol, octyldecanol, and other branched chain alcohols etc. may be mentioned.

As synthetic ester oils, isopropyl myristate, cetyl octanate, octyldodecyl myristate, isopropyl palmitate, butyl stearate, hexyl laurate, myristyl myristate, decyl oleate, hexyldecyl dimethyloctanate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkylglycol monoisostearate, neopentylglycol dicaproate, diisostearyl malate, glycerin di-2-heptyl undecanoate, trimethylopropane tri-2-ethylhexylate, trimethylopropane triisostearate, pentaerythritol tetra-2-ethylhexylate, glycerin tri-2-ethylhexylate, trimethylopropane triisostearate, cetyl-2-ethylhexanoate, 2-ethylhexyl palmitate, glycerin trimyristate, glyceride tri-2-heptylundecanoate, castor oil fatty acid methyl ester, oil oleate, cetostearyl alcohol, acetoglyceride, 2-heptylundecyl palmitate, diisobutyl adipate, N-lauroyl-L-glutamate-2-octyl dodecyl ester, di-2-heptylundecyl adipate, ethyl laurate, di-2-ethylhexyl sebatate, 2-hexyldecyl myristate, 2-hexyldecyl palmitate, 2-hexyldecyl adipate, diisopropyl sebatate, 2-ethylhexyl succinate, ethyl acetate, butyl acetate, amyl acetate, triethyl citrate, etc. may be mentioned.

As silicones, dimethyl polysiloxane, methylphenyl polysiloxane, methylhydrogen polysiloxane, and other chain like polysiloxanes, decamethyl polysiloxane, dodecamethyl polysiloxane, tetramethyltetrahydrogen polysiloxane, and other cyclic polysiloxanes, silicone resins forming 3D net structures, silicone rubber, etc. may be mentioned.

As anionic surfactants, for example, soap ingredients, sodium laurate, sodium palmitate, and other fatty acid soaps, sodium laurosulfate, potassium laurosulfate, and other higher alkyl sulfate ester salts, POE laurosulfate triethanol amine, sodium POE laurosulfate, and other alkyl ester sulfate ester salts, sodium lauroylsarcosine and other N-acylsarcosine acids, sodium N-myristyl-N-methyltaurine, sodium coconut oil fatty acid methyl tauride, sodium laurylmethyl tauride, and other higher fatty acid amide sulfonates, sodium POE oleyl ether phosphate, POE stearyl ether phosphate, and other phosphate ester salts, sodium di-2-ethylhexylsulfosuccinate, sodium monolauroylmonoethanol amide polyoxyethylene sulfosuccinate, sodium laurylpolypropylene glycol sulfosuccinate, and other sulfosuccinates, linear sodium dedecylbenzensulfonate, linear dodecylbenzensulfonate triethanol amine, linear dodecyl benzensulfate, and other alkylbenzensulfonates, sodium N-lauroylglutamate, disodium N-stearoylglutamate, monosodium N-myristoyl-L-glutamate, and other N-acylglutamates, sodium hardened castor oil fatty acid glycine sulfate and other higher fatty acid ester sulfate ester salts, Turkey red oil and other sulfated oils, POE alkyl ether carboxylic acid, POE alkylaryl ether carboxylate, α-olefinsulfates, higher fatty acid ester sulfonates, secondary alcohol sulfate ester salts, higher fatty acid alkylolamide sulfate ester salts, sodium lauroyl monoethanolamide succinate, N-palmitoyl asparaginate ditriethanol amine, sodium caseine, etc. may be mentioned.

As cationic surfactants, for example, stearyl trimethyl ammonium chloride, lauryl trimethyl ammonium chloride, and other alkyl trimethyl ammonium salts, distearyldimethyl ammonium chloride, dialkyldimethyl ammonium chloride salts, poly(N,N'-dimethyl-3,5-methylenepiperidinium) chloride, cetylpyridinium chloride and other alkyl pyridinium salts, alkyl quaternary ammonium salts, alkyl dimethylbenzyl ammonium salts, alkyl isoquinolinium salts, dialkyl morphonium salts, POE alkyl amines, alkyl amine salts, polyamine fatty acid derivatives, amyl alcohol fatty acid derivatives, benzalkonium chloride, benzethonium chloride, etc. may be mentioned.

As bipolar surfactants, for example, sodium 2-undecyl-N,N,N-(hydroxyethylcarboxymethyl)-2-imidazoline, 2-cocoyl-2-imidazoliniumhydroxide-1-carboxyethyloxy-2-sodium salt, and other imidazoline family bipolar surfactants, 2-heptadecyl-N-carboxymethyl-N-hydroxyethylimidazolinium betaine, lauryldimethylaminoacetate betaine, alkyl betaine, amide betaine, sulfo betaine, and other betaine family surfactants etc. may be mentioned.

As lyophilic nonionic surfactants, for example, sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, diglycerol sorbitan tetra-2-ethylhexylate, and other sorbitan fatty acid esters, glycerol cotton seed oil fatty acid mono ester, glycerin monoerucate, glycerin sesquioleate, glycerin monostearate, glycerin α,α-oleate pyroglutamate, monostearate glycerin malic acid and other glycerin polyglycerin fatty acids, propylene glycol monostearate and other propylene glycol fatty acid esters, hardened castor oil derivatives, glycerin alkyl ethers, polyoxyethylene methylpolysiloxane copolymers, etc. may be mentioned.

As hydrophilic nonionic surfactants, for example, POE sorbitan monooleate, POE-sorbitan monostearate, POE-sorbitan monoolate, POE-sorbitan tetraoleate, and other POE sorbitan fatty acid esters, POE-sorbite monolaurate, POE-sorbite monooleate, POE-sorbite pentaoleate, POE-sorbite monostearate, and other POE sorbite fatty acid esters, POE-glycerin monostearate, POE-glycerin monoisostearate, POE-glycerin triisostearate, and other POE glycerin fatty acid esters, POE monooleate, POE distearate, POE monodioleate, distearate ethylene glycol, and other POE fatty acid esters, POE lauryl ethers, POE oleyl ethers, POE stearyl ethers, POE behenyl ethers, POE2-octyldodecyl ethers, POE cholestanol ethers, and other POE alkyl ethers, POE octyl phenyl ethers, POE nonyl phenyl ethers, POE dinonyl phenyl ethers, and other POE alkyl phenyl ethers, Pluronic and other pluaronics, POE.POP cetyl ethers, POE.POP-2-decyltetradecyl ethers, POE.POP monobutyl ethers, POE-POP hydrated lanolin, POE.POP glycerin ethers, and other POE-POP alkyl ethers, Tetronic and other tetra-POE.tetra-POP ethylene diamine condensation products, POE castor oil, POE hardened castor oil, POE hardened castor oil monoisostearate, POE hardened castor oil triisostearate, POE hardened castor oil monopyroglutamate monoisostearate diester, POE hardened castor oil maleic acid and other POE castor oil hardened castor oil derivatives, POE sorbite beeswax and other POE beeswax lanolin derivatives, coconut oil fatty acid diethanol amide, laurate monoethanol amide, fatty acid isopropanol amide, and other alkanol amides, POE propylene glycol fatty acid esters, POE alkylamines, POE fatty acid amides, sucrose fatty acid esters, POE nonylphenyl formaldehyde condensation products, alkylethoxydimethylamineoxide, trioleylphosphoric acid etc. may be mentioned.

As preservatives, methylparaben, ethylparabene, butylparaben, etc. may be mentioned.

As metal ion Chelates, sodium edetate salts, EDTA, etc. may be mentioned.

As natural water soluble polymers, arabia gum, tragacanth gum, galactan, guar gum, carob gum, karaya gum, carragheein, pectin, agar, quince seed, algae colloid (seaweed extract), starch (rice, corn, potato, wheat), glycyrrhizic acid, and other plant family polymers, xanthane gum, dextran, succinoglutan, pullulan, and other microorganism family polymers, collagenous protein, caseine, albumin, gelatin, and other animal family polymers etc. may be mentioned.

As semisynthesized water soluble polymers, carboxymethyl starch, methylhydroxpropyl starch, or other starch family polymers, methyl cellulose, nitro cellulose, ethyl cellulose, methylhydroxypropyl cellulose, hydroxyethyl cellulose, sodium cellulose sulfate, hydroxypropyl cellulose, sodium carboxymethyl cellulose (CMC), crystalline cellulose, cellulose powder, and other cellulose family polymers, sodium alginate, alginate propylene glycol esters, and other alginate family polymers etc. may be mentioned.

As synthesized water soluble polymers, a polyvinyl alcohol, polyvinylmethyl ether, polyvinylpyrrolidone, carboxyvinyl polymer (carbopol), alkyl modified carboxyvinyl polymer, or other vinyl family polymer, polyethylene glycol 2000, 4000, 6000, or other polyoxyethylene family polymer, polyoxyethylene polyoxypropylene copolymer family polymer, sodium polyacrylate, polyethylene acrylate, polyacryl amide, or other acryl family polymer, polyethylene imine, cationic polymer, etc. may be mentioned.

As inorganic water soluble polymers, bentonite, AlMg silicate (bee gum), laponite, hectonite, inorganic silicic acid, etc. may be mentioned.

As the thickeners, carragheenin, karaya gum, tragacanth gum, carob gum, quince seed (Marumero), caseine, dextrin, gelatin, sodium pectinate, sodium alginate, methyl cellulose, ethyl cellulose, CMC, hydroxyethyl cellulose, hydroxypropyl cellulose, PVA, PVM, PVP, sodium polyacrylate, carboxyvinyl polymer, loqust bean gum, guar gum, tamarind gum, dialkyldimethyl ammonium sulfate cellulose, xanthane gum, aluminum magnesium silicate, bentonite, hectonite, etc. may be mentioned.

As powder components, talc, kaolin, mica, sericite, dolomite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal salts of tungstenic acid, magnesium, silica, zeolite, barium sulfate, sintered calcium sulfate (sintered gypsum), calcium phosphate, fluorapatite, hydroxyapatite, ceramic powder, metal soap (zinc myristate, calcium palmitate, ammonium stearate), boronitride, and other inorganic powders, polyamide resin powder (nylon powder), polyethylene powder, methyl polymethacrylate powder, polytetrafluoroethylene powder, cellulose powder, and other organic powders, titanium dioxide, zinc oxide, and other inorganic white pigments, iron oxide (bengara), iron titanate, and other inorganic red pigments, γ-iron oxide and other inorganic brown pigments, yellow iron oxide, yellow earth, and other inorganic yellow pigments, black iron oxide, carbon black, lower titanium oxide, and other inorganic black pigments, mango violet, cobalt violet, and other inorganic violet pigments, chromium oxide, chromium hydroxide, cobalt titanate, and other inorganic green pigments, prussian blue, ultramarine, and other inorganic blue pigments, titanium oxide coated talc, colored titanium oxide coated mica, bismuth oxichloride, fish scales, and other pearl pigments, aluminum powder, copper powder, and other metal powder pigments, Red No. 201, Red No. 202, Red No. 204, Red No. 205, Red No. 220, Red No. 226, Red No. 228, Red No. 405, Orange No. 203, Orange No. 204, Yellow No. 204, Yellow No. 401, Blue No. 404, and other organic pigments, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, Blue No. 1, and other zirconium, barium, or aluminum lakes and other organic pigments, chlorophyll, β-carotine, and other natural colors, perfumes, water, alcohol, titanium yellow, Safflower Yellow, Safflower Red, and other coloring agents, etc. may also be suitably blended into the anti-aging cosmetic composition of the present invention if necessary.

EXAMPLES

Next, the anti-aging cosmetic composition of the present invention will be explained in further detail based on Examples. The present invention is not however limited to these Examples.

Preparation Example 1 (Production of Enzymolzed Solution of Alkali Extract of Hypoallergenic Rice)

100 g of rice was immersed in an aqueous solution of sodium hydrogencarbonate adjusted to a pH of 8 to 9.5 mg of Actinase (optimal pH of 8.0) was added and the result treated at 30° to 40° C. for 24 hours to obtain hypoallergenic rice. Note that the obtained hypoallergenic rice had about 50 percent by weight of the globulin, a type of allergen, decomposed and removed.

Next, 100 g of the above hypoallergenic rice was added to 1000 ml of refined water. The mixture was adjusted to a pH of 11 to 13 by an aqueous solution of 0.1N sodium hydroxide The rice was immersed and extracted at room temperature for about 24 hours to obtain about 500 ml of an extract (solid content: about 5 wt %).

Next, 5 mg of Actinase (optimal pH 8.0) was added to the extract and treatment was performed at 30° to 40° C. for 1 to 2 hours. Next, 5 mg of pepsin (optimal pH 2.0) was added and the treatment performed at 30° to 40° C. for 1 to 2 hours. Finally, 5 mg of trypsin (optimal pH 8.0) was added and the treatment performed at 30° to 40° C. for 1 to 2 hours.

Note that when adding the enzymes, the extract was adjusted to the optimal pH of the enzymes.

The result was filtered to obtain about 300 ml of a light yellow transparent enzymolzed solution (solid content: about 2 wt %).

Preparation Example 2 (Production of Enzymolzed Solution of Alkali Extract of Hypoallergenic Rice)

The same procedure was followed as in Preparation Example 1, except that use was made of papain (optimal pH 7.0) instead of the pepsin in Preparation Example 1, to obtain about 300 ml of a light yellow transparent enzymolzed solution (solid content: about 2 wt %).

Preparation Example 3 (Preparation of Freeze-Dried Treated Enzymolyzed Alkali Extract of Hypoallergenic Rice)

100 g of the enzymolyzed solution obtained in Preparation Example 1 was concentrated and then vacuum freeze-dried to obtain about 2 g of an enzymolyzed dried powder.

Preparation Example 4 (Production of Spray Dried Enzymolyzed Alkali Extract of Hypoallergenic Rice)

250 g of the enzymolyzed solution obtained in Preparation Example 2 was spray dried to obtain about 5 g of enzymolyzed dried powder.

Test Examples I-1 to I-5

The enzymolyzed solution obtained in Preparation Example 1 was used as a sample on which the tests shown below were performed:

1.0 ml of 0.5M ethanol linolate, 10 ml of 0.2M phosphate buffer (pH 7.0), and 9.0 ml of ethanol were accurately weighed and sufficiently agitated in a stoppered triangular flask. To this was added the 5.0 ml of the above accurately weighed enzymolyzed solution. The mixture was then fully agitated.

Next, 0.1 ml each of the solution just after the preparation and the solution after being left standing in a 40° C. constant temperature tank for 7 days were accurately weighed. To each were added 4.7 ml of 75% ethanol, 0.1 ml of 30 percent solution of ammonium thiocyanate, and 0.1 ml of a 3.5 percent hydrogen chloride solution of 0.02M ferric chloride. The mixtures were fully mixed and agitated, then the absorptions at OD. 500 nm after exactly 3 minutes were measured and the peroxide value indexes were found based on the following formula:

Peroxide value index $(\%) = (T_7 - T_0)/(B_7 - B_0) \times 100$

Note that in the formula, $T_7$ is the absorption of the solution to which the enzymolyzed solution after the elapse of 7 days from the start of the test was added, $B_7$ is the absorption of the solution to which refined water was added instead of the enzymolyzed solution after the elapse of 7 days from the start of the test, $T_0$ is the absorption of the solution to which the enzymolyzed solution was added immediately after the start of the test, and $B_0$ is the absorption of the solution to which refined water was added instead of the enzymolyzed solution immediately after the start of the test.

Further, a solution prepared in the same way using refined water instead of the enzymolyzed solution was used as a blank. The results are shown in Table I-1.

TABLE I-1

|  | Sample containing enzymolyzed solution | Blank |
| --- | --- | --- |
| Peroxide value index (%) | 0.5 | 100.0 |

As clear from the results shown in Table I-1, the enzymolyzed solution obtained in Preparation Example 1 exhibits a superior action in suppressing the production of peroxide lipids.

Test Example I-2 (SOD-Like Activation Action)

0.15 ml of 1M Tris.HCl buffer, 0.30 ml of 1 mM ethylenediaminetetrachloric acid (hereinafter referred to as "EDTA"), 0.20 ml of 0.2 mM cytochrome C solution, and 0.30 ml of 1 mM xanthine solution were accurately weighed and fully agitated in a stoppered triangular flask. To this were added accurately weighed 0.10 ml of the enzymolyzed solution, 0.05 ml of a xanthine oxidase solution (0.01 U/0.01 ml), and 1.90 ml of refined water, then the absorptions at OD. 550 nm after the elapse of every 60 seconds was measured. The results are shown in the Graph A of FIG. 1.

Further, a solution prepared in the same way using refined water instead of the enzymolyzed solution was used as a blank. The results are shown in the Graph B of FIG. 1.

As clear from the results shown in FIG. 1, the enzymolyzed solution obtained in Preparation Example 1 exhibits a superior SOD-like activation action.

Test Example I-3 (Action Promoting Synthesis of Collagenous protein)

An Eagle minimum essential medium (hereinafter referred to as "MEM") containing 5% by volume of fetal calf serum (hereinafter referred to as "FCS") was used as the basic medium and human dermis-derived fibroblasts were used as the cells.

The cells were cultured in the basic medium for a predetermined period, then a medium including 5% by volume of the above enzymolyzed solution was added and the result was cultured at 37° C. for 5 days. During that time, the medium was replaced once. Further, the result of culturing using only the basic medium was used as a blank.

The amount of collagenous protein and the amount of non-collagenous protein per $10^4$ cells were measured for the fibroblasts cultured by the above procedure to investigate the action in promoting the synthesis of collagenous protein. Note that the collagenous protein was quantized using the collagenous protein stain kit made by Cosmo Bio Co. The results are shown in FIG. 2.

As clear from the results shown in FIG. 2, the enzymolyzed solution obtained in Preparation Example 1 exhibits a superior action promoting the synthesis of collagenous protein.

Test Example I-4 (Action Restoring UV Damage)

An Eagle MEM containing 10% by volume of FCS was used as the basic medium and human dermis-derived fibroblasts were used as the cells.

The cells were cultured in the basic medium for a predetermined period, then a medium including 10% by volume of the above enzymolyzed solution was added while irradiating UV rays by a UV lamp (Toshiba Health Ray Lamp, made by Toshiba Corporation, output of 30 W) and the result was cultured at 37° C. for 10 days. During that time, the medium was replaced twice. Further, the result of culturing using only the basic medium was used as a blank.

The fibroblasts cultured by the above procedure were measured as to the cell count and the reanimated cell count by isolating the cells using trypsin EDTA after culturing so as to investigate the action in restoring damage caused by UV rays. The results are shown in FIG. 3.

As clear from the results shown in FIG. 3, the enzymolyzed solution obtained in Preparation Example 1 exhibits a superior action restoring damage to cells caused by UV rays.

Test Example I-5 (Storage Stability)

The above enzymolyzed solution was filled into a 50 ml volume screw tube and stored at 40° C. for 90 days at constant temperature conditions.

The coloring and presence of precipitates in the enzymolyzed solution after the elapse of 10 days, 20 days, 30 days, 60 days, and 90 days from the start of the test were visually observed. Further, the enzymolyzed solution obtained using normal rice instead of hypoallergenic rice in Preparation Example 1 was used as a blank and was stored in the same way as the enzymolyzed solution obtained in Preparation Example 1 to visually investigate the coloring and presence of precipitates. The results are shown in Table I-2.

TABLE I-2

| Number of days of storage elapsed (days) | | 10 | 20 | 30 | 60 | 90 |
|---|---|---|---|---|---|---|
| Enzymolyzed solution obtained in Preparation Example 1 | Coloring | No | No | No | No | No |
| | Precipitates | No | No | No | No | No |
| Enzymolyzed solution of rice (blank) | Coloring | No | No | No | No | Yes |
| | Precipitates | Yes | Yes | Yes | Yes | Yes |

As clear from the results shown in Table I-2, the enzymolyzed solution obtained in Preparation Example 1 did not exhibit any coloring or precipitates over the long period of 90 days, so it was learned that the quality did not change and the storage stability was excellent.

Formulation Examples I-1 to I-13 and Comparative Formulation Examples I-1 to I-13

| | Parts |
|---|---|
| Components (A) | |
| Liquid paraffin | 5.0 |
| Hexalane (glyceryl trioctanate, made by Kyoei Chemical Industry) | 4.0 |
| Paraffin | 5.0 |
| Cetanol | 2.0 |
| Glyceryl monostearate | 2.0 |
| Polyoxyethylene (20) sorbitan monostearate | 6.0 |
| Butylparaben | 0.1 |
| Components (B) | |
| Enzymolyzed solution obtained in Preparation Example 1 | 20.0 |
| Glycerol | 5.0 |
| Sodium carboxymethylcellulose | 0.1 |
| Methylparaben | 0.1 |
| Moiston C (natural moisturizing factor, made by Kyoei Chemical Industry) | 1.0 |
| Purified water | Balance to 100 parts |
| Component C | |
| Fragrance | 0.3 |

The above component (A) and component (B) were each warmed to at least 80° C., then the component (A) and component (B) were mixed and stirred. The result was cooled to 50° C., then the component (C) was added and the mixture was further stirred and mixed to prepare a homogeneous cream.

Formulation Example I-2 (Emulsion)

| | Parts |
|---|---|
| Components (A) | |
| Liquid paraffin | 6.00 |
| Hexalane (glyceryl trioctanate, made by Kyoei Chemical Industry) | 4.00 |
| Jojoba oil | 1.00 |
| Polyoxyethylene (20) sorbitan monostearate | 2.00 |
| Soybean lecithin oil | 1.50 |
| Methylparaben | 0.15 |
| Ethylparaben | 0.03 |
| Components (B) | |
| Enzymolyzed solution obtained in Preparation Example 1 | 30.00 |
| Glycerol | 3.00 |
| 1,3-butylene glycol | 2.00 |
| Sodium carboxymethylcellulose | 0.30 |
| Sodium hyalonate | 0.01 |
| Purified water | Balance to 100.0 parts |
| Component (C) | |
| Fragrance | 0.05 |

The above component (A) and component (B) were each warmed to 80° C., then the component (A) and component (B) were mixed and stirred. The result was cooled to 50° C., then the component (C) was added and the mixture was further stirred and mixed to prepare a homogeneous emulsion.

Formulation Example I-3 (Lotion)

| Component | Parts |
|---|---|
| L-ascorbyl magnesium phosphate | 2.0 |
| Ethanol | 10.0 |
| Glycerol | 3.0 |
| 1,3-butylene glycol | 2.0 |
| Methylparaben | 0.2 |
| Citric acid | 0.1 |
| Sodium citrate | 0.3 |
| Carboxyvinyl polymer | 0.1 |
| Water soluble placenta extract | 1.0 |
| Enzymolyzed solution obtained in Preparation Example 1 | 10.0 |
| Perfume | q.s. |
| Purified water | Balance to 100.0 parts |

The above ingredients were mixed to prepare a homogeneous lotion.

Formulation I-4 (Essence)

| Components | Parts |
|---|---|
| Ethanol | 10.0 |
| Glycerol | 5.0 |
| 1,3-butylene glycol | 1.0 |
| Oleyl alcohol | 0.1 |
| Polyoxyethylene sorbitan monostearate ester (20EO) | 2.0 |
| Methylparaben | 0.2 |
| Citric acid | 0.1 |
| Sodium citrate | 0.3 |
| Carboxyvinyl polymer | 0.3 |
| Enzymolyzed solution obtained in Preparation Example 1 | 1.0 |

-continued

| Components | Parts |
| --- | --- |
| Perfume | q.s. |
| Water soluble collagenous protein | 1.0 |
| Purified water | Balance to 100.0 parts |

The above ingredients were mixed to prepare a homogeneous essence.

Formulation Example I-5 (Pack)

| Components | Parts |
| --- | --- |
| Polyvinyl alcohol | 15.0 |
| Hydromethylcellulose | 5.0 |
| Propylene glycol | 5.0 |
| Ethanol | 10.0 |
| Methylparaben | 0.1 |
| Enzymolyzed solution obtained in Preparation Example 2 | 10.0 |
| Perfume | |
| Purified water | Balance to 100.0 parts |

The above ingredients were mixed to prepare a homogeneous pack.

Formulation I-6 (Facial Cleanser)

| Components | Parts |
| --- | --- |
| Stearic acid | 15.0 |
| Lauric acid | 5.0 |
| Myristic acid | 15.0 |
| Glyceryl monostearate | 4.0 |
| Sodium hydroxide | 7.0 |
| Glycerol | 8.0 |
| Enzymolyzed solution obtained in Preparation Example 2 | 10.0 |
| Methylparaben | 0.2 |
| Purified water | Balance to 100.0 parts overall |

The above ingredients were warmed to 85° C. then mixed to prepare a homogeneous facial cleanser.

Formulation Example I-7 (Shampoo)

| Components | Parts |
| --- | --- |
| Sodium paraoxyethylene lauryl ether sulfate | 25.0 |
| Triethanolamine lauryl sulfate | 15.0 |
| Coconut oil fatty acid diethanol amide | 4.0 |
| Monostearate ethylene glycol | 1.50 |
| Bisodium edetate | 0.05 |
| Methylparaben | 0.10 |
| Perfume | q.s. |
| Yellow No. 4 | q.s. |
| Enzymolyzed solution obtained in Preparation Example 2 | 50.0 |
| Purified water | Balance to 100.0 parts |

The above ingredients were warmed to at least 80° C., then mixed and stirred to prepare a homogeneous shampoo.

Formulation Example I-8 (Rinse)

| Components | Parts |
| --- | --- |
| Stearyl trimethylammonium chlorate | 1.5 |
| Cetanol | 2.0 |
| 2-octyl dodecanol | 1.0 |
| Cationized cellulose | 0.5 |
| Polyoxyethylene cetyl ether | 1.0 |
| Propylene glycol | 5.0 |
| Methylparaben | 0.1 |
| Perfume | q.s. |
| Enzymolyzed solution obtained in Preparation Example 2 | 50.0 |
| Purified water | Balance to 100.0 parts |

The ingredients were warmed to at least 80° C., then mixed and stirred to prepare a homogeneous rinse.

Formulation I-9 (Treatment)

| Components | Parts |
| --- | --- |
| Stearyl trimethyl ammonium chloride | 6.0 |
| Polyvinylpyrrolidone | 4.0 |
| Glycerol | 1.0 |
| Ethylparaben | 0.1 |
| Enzymolyzed solution obtained in Preparation Example 1 | 50.0 |
| Purified water | Balance to 100.0 parts |

The components were warmed to 80° C., then were mixed and stirred to prepare a homogeneous treatment.

Formulation I-10 (Hair Lotion)

| Components | Parts |
| --- | --- |
| Ethanol | 60.0 |
| Polyoxypropylene butyl ether (40EO) | 20.0 |
| Diisopropanol amine | 2.0 |
| Edetate salt | q.s. |
| Perfume | q.s. |
| Enzymolyzed solution obtained in Preparation Example 2 | Balance to 100.0 parts |

The above components were mixed to prepare a homogeneous hair lotion.

Formulation I-11 (Bath Additive)

| Components | Parts |
| --- | --- |
| Sodium sulfate | 35.0 |
| Sodium hydrogencarbonate | 52.0 |
| Boric acid | 2.0 |
| Sodium carboxylmethylcellulose | 1.0 |
| Red No. 201 | q.s. |
| Perfume | q.s. |
| Dried powder obtained in Preparation Example 3 | Balance to 100.0 parts |

Preparation Example 3 Balance to 100.0 parts

The above components were mixed to prepare a homogeneous bath additive.

Formulation Example I-12 (Lipstick)

| | Parts |
|---|---|
| Components (A) | |
| Castor oil | 50.0 |
| Octyl dodecanol | 4.0 |
| Lanolin | 5.0 |
| Liquid lanolin | 5.0 |
| Beeswax | 4.0 |
| Ozokerite | 7.0 |
| Candelilla wax | 2.0 |
| Carnauba wax | 1.0 |
| Components (B) | |
| Titanium oxide | 1.0 |
| Color (Red No. 201 etc.) Total | 4.0 |
| Dried powder obtained in Preparation Example 4 | Balance to 100.0 parts |
| Components (C) | |
| Fragrance | q.s. |

The above component (A) and component (B) were each warmed, then the component (A) and component (B) were mixed and stirred. The result was rewarmed, the component (C) was added, then the result was poured into a mold and quickly cooled to prepare the lipstick.

Formulation Example I-13 (Liquid Foundation)

| | Parts |
|---|---|
| Components (A) | |
| Stearic acid | 2.4 |
| Propylene glycol monostearate | 2.0 |
| Cetostearyl alcohol | 0.2 |
| Liquid lanolin | 2.0 |
| Liquid paraffin | 3.0 |
| Isopropyl myristate | 8.5 |
| Propylparaben | q.s. |
| Components (B) | |
| Enzymolyzed solution obtained in Preparation Example 2 | Balance to 100.0 parts |
| Sodium carboxymethylcellulose | 0.2 |
| Bentonite | 0.5 |
| Propylene glycol | 4.0 |
| Triethanol amine | 1.1 |
| Methylparaben | q.s. |
| Components (C) | |
| Titanium oxide | 8.0 |
| Talc | 4.0 |
| Coloring pigment | q.s. |

The above component (A) and component (B) were each warmed, then the component (A) and component (B) were mixed and stirred. The result was rewarmed, the component (C) were added, and the result was poured into a mold and stirred until reaching room temperature to prepare a liquid foundation.

Comparative Formulation Example I-1 (Cream)

The same procedure was followed as in Formulation Example 1 to prepare a cream except for the use of purified water instead of the enzymolyzed solution obtained in Preparation Example 1.

Comparative Formulation Example I-2 (Emulsion)

The same procedure was followed as in Formulation Example I-2 to prepare an emulsion except for the use of purified water instead of the enzymolyzed solution obtained in Preparation Example 1.

Comparative Formulation Example I-3 (Lotion)

The same procedure was followed as in Formulation Example I-3 to prepare a lotion except for the use of purified water instead of the enzymolyzed solution obtained in Preparation Example 1.

Comparative Formulation Example I-4 (Essence)

The same procedure was followed as in Formulation Example I-4 to prepare an essence except for the use of purified water instead of the enzymolyzed solution obtained in Preparation Example 1.

Comparative Formulation Example I-5 (Pack)

The same procedure was followed as in Formulation Example I-5 to prepare a pack except for the use of refined water instead of the enzymolyzed solution obtained in Preparation Example 2.

Comparative Formulation Example I-6 (Facial Cleanser)

The same procedure was followed as in Formulation Example I-6 to prepare a facial cleanser except for the use of refined water instead of the enzymolyzed solution obtained in Preparation Example 2.

Comparative Formulation Example I-7 (Shampoo)

The same procedure was followed as in Formulation Example I-7 to prepare a shampoo except for the use of refined water instead of the enzymolyzed solution obtained in Preparation Example 2.

Comparative Formulation Example I-8 (Rinse)

The same procedure was followed as in Formulation Example I-8 to prepare a rinse except for the use of refined water instead of the enzymolyzed solution obtained in Preparation Example 2.

Comparative Formulation Example I-9 (Hair Treatment)

The same procedure was followed as in Formulation Example I-9 to prepare a hair treatment except for the use of refined water instead of the enzymolyzed solution obtained in Preparation Example 1.

Comparative Formulation Example I-10 (Hair Styling Product)

The same procedure was followed as in Formulation Example I-10 to prepare a hair styling product except for the use of purified water instead of the enzymolyzed solution obtained in Preparation Example 2.

Comparative Formulation Example I-11 (Bath Additive)

The same procedure was followed as in Formulation Example I-11 to prepare a bath additive except for the use of sodium sulfate instead of the dried powder obtained in Preparation Example 3.

Comparative Formulation Example I-12 (Lipstick)

The same procedure was followed as in Formulation Example I-12 to prepare a lipstick except for the use of nylon powder instead of the dried powder obtained in Preparation Example 3.

Comparative Formulation Example I-13 (Liquid Foundation)

The same procedure was followed as in Formulation Example I-13 to prepare a liquid foundation except for the use of purified water instead of the enzymolyzed solution obtained in Preparation Example 2.

Example I-1

The cosmetics obtained in Formulation Example I-1 to I-6 and Comparative Formulation Example I-1 to I-6 were subjected to a monitor test as shown below. The results are shown in Table I-3.

Monitor test

One hundred healthy adult women of age 25 to 57 extracted at random were used as test subjects. The cosmetics were used on the skin of the face every day for one month, then a study was made of the (a) the effect of improvement on the lack of luster and stains of the skin, (b) the effect of improvement on small wrinkles, and (c) the effect of reduction of the variation in area between corneocytes.

(a) Effect of improvement on lack of luster and stains of skin

The state of the skin was observed visually and evaluated based on the following evaluation criteria.

Evaluation Criteria

A: Extremely improved

B: Improved

C: No change

D: Slight noticeable

E: Noticeable (b) Effect of improvement on small wrinkles

The state of the skin was observed visually and evaluated based on the following evaluation criteria.

Evaluation Criteria

A: Completely disappeared

B: Somewhat reduced

C: No change

D: Slightly increased

E: Increased (c) Effect of reduction of variation in area between corneocytes

A two-sided tape (Nicetac, made by Nichiban) was used to isolate 30 corneal cells from the left cheek of the face of the test subject by the tape stripping method and the area of each of the cells was measured. The standard deviation was calculated for the cell areas obtained and the evaluation made based on the following evaluation criteria.

Evaluation Criteria

A: Standard deviation reduced 50%

B: Standard deviation reduced 25%

C: No change

D: Standard deviation increased 25%

E: Standard deviation increased 50%

Note that in the monitor test, when using the cosmetics obtained in Formulation Examples I-1 to I-6, not even one test subject experienced an abnormality of the skin.

Further, none of the cosmetics obtained in Formulation Examples I-1 to I-6 showed any change in state over one month.

TABLE I-3

| Formulation Ex. No. | Evaluation of effect on lack of luster and stains of skin (persons) | | | | | Evaluation of effect on small wrinkles (persons) | | | | | Evaluation of effect on variation of area between corneal cells (persons) | | | | |
|---|---|---|---|---|---|---|---|---|---|---|---|---|---|---|---|
| | A | B | C | D | E | A | B | C | D | E | A | B | C | D | E |
| Ex. I-1 | 82 | 17 | 1 | 0 | 0 | 87 | 10 | 3 | 0 | 0 | 80 | 9 | 8 | 2 | 1 |
| Ex. I-2 | 80 | 13 | 5 | 1 | 1 | 79 | 13 | 6 | 1 | 1 | 76 | 13 | 8 | 2 | 1 |
| Ex. I-3 | 77 | 14 | 4 | 3 | 2 | 78 | 16 | 3 | 2 | 1 | 77 | 14 | 2 | 6 | 1 |
| Ex. I-4 | 75 | 19 | 2 | 2 | 2 | 81 | 13 | 4 | 1 | 1 | 75 | 17 | 7 | 1 | 0 |
| Ex. I-5 | 83 | 131 | 3 | 1 | 0 | 79 | 12 | 7 | 2 | 0 | 80 | 12 | 5 | 2 | 1 |
| Ex. I-6 | 79 | 5 | 4 | 1 | 1 | 77 | 16 | 6 | 1 | 0 | 80 | 10 | 5 | 3 | 2 |
| Comp. Ex. I-1 | 9 | 20 | 24 | 40 | 7 | 18 | 15 | 25 | 34 | 8 | 8 | 21 | 28 | 26 | 17 |
| Comp. Ex. I-2 | 8 | 201 | 39 | 25 | 8 | 14 | 23 | 29 | 30 | 4 | 13 | 19 | 28 | 21 | 19 |
| Comp. Ex. I-3 | 7 | 3 | 40 | 31 | 9 | 20 | 21 | 27 | 18 | 14 | 9 | 21 | 28 | 22 | 20 |
| Comp. Ex. I-4 | 7 | 18 | 43 | 25 | 7 | 15 | 28 | 37 | 17 | 3 | 9 | 11 | 37 | 27 | 16 |
| Comp. Ex. I-5 | 10 | 24 | 27 | 32 | 7 | 16 | 26 | 29 | 18 | 11 | 12 | 18 | 28 | 23 | 19 |
| Comp. Ex. I-6 | 13 | 20 | 33 | 26 | 8 | 20 | 18 | 21 | 30 | 11 | 14 | 13 | 32 | 37 | 4 |

As clear from the results shown in Table I-3, when using the cosmetics obtained in Formulation Examples I-1 to I-6, the variation in area between corneal cells was remarkably reduced and the lack of luster and stains or small wrinkles of the skin were improved.

Example I-2

The hair cosmetics obtained in Formulation Examples I-7 to I-10 and Comparative Formulation Examples I-7 to I-10 were subjected to a half head test as shown below. The results are shown in Table I-4.

Half head test

Twenty healthy adult women of age 25 to 60 extracted at random were used as test subjects. The hair cosmetics were used on the hair once a day for 30 days, then an evaluation was made of the (d) split ends, (e) body, and (f) gloss of the hair based on the following evaluation criteria:

(d) Evaluation Criteria of Split Ends

A: Disappeared

B: Reduced

C: No change

D: Slightly increased
E: Increased
(e) Evaluation Criteria of Body
A: Greater body
B: Slightly more body
C: No change
D: Slightly less body
E: Less body
(f) Evaluation Criteria of Gloss
A: Improved
B: Slightly improved
C: No change
D: Slightly worse
E: Worse Note that in the half head test, when using the hair cosmetics obtained in Formulation Examples I-7 to I-10, not even one test subject experienced an abnormality of the hair or scalp.

Further, none of the hair cosmetics obtained in Formulation Examples I-7 to I-10 showed any change in state over 30 days.

C: No change
D: Standard deviation increased 25%
E: Standard deviation increased 50%

Note that in the monitor test, when using the bath additive obtained in Formulation Example I-11, not even one test subject experienced an abnormality of the skin.

Further, the bath additive obtained in Formulation Example I-11 did not show any change in state over 4 weeks.

TABLE I-5

| Formulation Ex. No. | Evaluation of effect on variation of area between corneal cells (persons) | | | | |
|---|---|---|---|---|---|
| | A | B | C | D | E |
| Ex. I-11 | 15 | 4 | 1 | 0 | 0 |
| Comp. Ex. I-11 | 1 | 2 | 7 | 6 | 4 |

As clear from the results shown in Table I-5, when using the bath additive obtained in Formulation Example I-11, the variation in area between corneocytes was remarkably reduced.

TABLE I-4

| Formulation Ex. No. | Evaluation of split ends (persons) | | | | | Evaluation of body (persons) | | | | | Evaluation of gloss (persons) | | | | |
|---|---|---|---|---|---|---|---|---|---|---|---|---|---|---|---|
| | A | B | C | D | E | A | B | C | D | E | A | B | C | D | E |
| Ex. I-7 | 8 | 6 | 5 | 1 | 0 | 13 | 6 | 1 | 1 | 0 | 7 | 5 | 6 | 2 | 0 |
| Ex. I-8 | 9 | 7 | 3 | 1 | 0 | 13 | 4 | 2 | 1 | 0 | 8 | 4 | 6 | 1 | 1 |
| Ex. I-9 | 10 | 6 | 3 | 0 | 1 | 11 | 6 | 2 | 1 | 0 | 7 | 6 | 4 | 2 | 1 |
| Ex. I-10 | 8 | 6 | 4 | 1 | 1 | 10 | 7 | 2 | 1 | 0 | 9 | 3 | 6 | 1 | 1 |
| Comp. Ex. I-7 | 1 | 2 | 4 | 3 | 10 | 0 | 1 | 6 | 8 | 5 | 1 | 1 | 5 | 6 | 7 |
| Comp. Ex. I-8 | 2 | 1 | 3 | 4 | 10 | 0 | 1 | 7 | 8 | 6 | 1 | 3 | 3 | 6 | 7 |
| Comp. Ex. I-9 | 1 | 3 | 3 | 9 | 4 | 0 | 2 | 5 | 5 | 8 | 0 | 1 | 4 | 6 | 9 |
| Comp. Ex. I-10 | 0 | 1 | 2 | 9 | 8 | 1 | 3 | 4 | 4 | 8 | 1 | 1 | 2 | 8 | 5 |

As clear from the results shown in Table 4, when using the hair cosmetics obtained in Formulation Examples I-7 to I-10, the split ends, body, and gloss of the hair were remarkably reduced or improved.

Example I-3

The bath additive obtained in Formulation Example I-11 and Comparative Formulation Example I-11 were subjected to a monitor test as shown below. The results are shown in Table I-5.

Monitor test

Twenty healthy adult women of age 27 to 59 extracted at random were used as test subjects. The bath additive was used for 4 weeks, then a study was made of the (g) the effect of reduction of the variation in area between corneocytes. Note that 25 g of the bath additive was added to and dissolved in 200 liters of hot water.

(g) Effect of reduction of variation in area between corneocytes

The same procedure was followed as in Example I-1, except for the use of 30 cells from the left side stomach of the test subjects, to calculate the standard deviation and make the evaluation based on the following evaluation criteria.

Evaluation Criteria
A: Standard deviation reduced 50%
B: Standard deviation reduced 25%

Example I-4

The cosmetics obtained in Formulation Examples I-12 to I-13 and Comparative Formulation Examples I-12 to I-13 were subjected to a monitor test as shown below. The results are shown in Table I-6.

Monitor test

One hundred healthy adult women of age 25 to 57 extracted at random were used as test subjects. A study was made of the (h) the effect of improvement on small wrinkles after the cosmetics were used on the skin of the face every day for one month and (i) the effect of reduction of the variation in area between corneocytes after the cosmetics were used on the lips or the skin of the cheek of the face every day for one month.

(h) Effect of improvement on small wrinkles

The state of the skin was observed visually and evaluated based on the following evaluation criteria.

Evaluation Criteria
A: Completely disappeared
B: Somewhat reduced
C: No change
D: Slightly increased
E: Increased (i) Effect of reduction of variation in area between corneal cells The same procedure was used as in Example I-1, except for using 30 cells from the lips of the test subjects for the cosmetics of Formulation Example I-12 and Comparative Formulation Example I-12 and 30 cells from the left cheek of the face of the test subjects for the cosmetics of Formulation Example I-13 and Comparative Formulation Example I-13, to calculate the standard deviation and make an evaluation based on the following evaluation criteria.

Evaluation Criteria
A: Standard deviation reduced 50%
B: Standard deviation reduced 25%
C: No change
D: Standard deviation increased 25%
E: Standard deviation increased 50%

Note that in the monitor test, when using the cosmetics obtained in Formulation Examples I-12 to I-13, not even one test subject experienced an abnormality of the skin.

Further, none of the cosmetics obtained in Formulation Examples I-12 to I-13 changed in state after one month.

TABLE I-6

| Formulation Ex. No. | Evaluation of effect on small wrinkles (persons) | | | | | Evaluation of effect on variation of area between corneal cells (persons) | | | | |
|---|---|---|---|---|---|---|---|---|---|---|
| | A | B | C | D | E | A | B | C | D | E |
| Ex. I-12 | — | — | — | — | — | 75 | 19 | 5 | 1 | 0 |
| Ex. I-13 | 88 | 9 | 2 | 1 | 0 | 77 | 17 | 3 | 2 | 1 |
| Com Ex. I-12 | — | — | — | — | — | 9 | 24 | 29 | 29 | 9 |
| Com Ex. I-13 | 18 | 23 | 30 | 20 | 9 | 9 | 21 | 39 | 25 | 6 |

As clear from the results shown in Table I-6, when using the cosmetics obtained in Formulation Examples I-12 to I-13, the variation in the area between corneocytes is remarkably reduced and small wrinkles are improved.

As explained above, the enzymolyzed substance obtained by treating the alkali extract of the hypoallergenic rice used in the present invention with one or more types of enzymes has all of the effects serving as indicators of an anti-aging effect on the skin demanded in the past, for example, an action suppressing the production of peroxide lipids, an SOD-like activation action, an action promoting the synthesis of collagenous protein, and an action restoring UV damage, so the anti-aging cosmetic of the present invention in which this enzymolyzed substance is blended has the superior effects of not only giving a simple moisturizing effect, but also restoring the turnover of the human skin to normal, reducing the variation of the area between corneal cells and preventing lack of luster and stains on the skin, and activating the cells of the skin so as to improve the small wrinkles. Further, when made into a hair cosmetic, it has the effect of reducing split ends and improving the body, gloss, etc.

Further, the enzymolyzed substance used in the present invention is obtained from hypoallergenic rice obtained by treating rice in advance with a proteinase, so not only has a low allergenicity, but also has a high stability of quality. The anti-aging cosmetic of the present invention in which this enzymolyzed substance is blended exhibits a superior effect of storage stability.

Test Examples II-1 to II-3

The enzymolzed solution obtained in Preparation Example 1 was used as a sample for the performance of the tests shown below:

Test Example II-1 (Effect Preventing Crosslinking of Collagenous protein by UV Rays)

(1) First, an explanation will be made of the method for finding the ratio of crosslinking of collagenous protein caused by UV rays.

Collagenous protein was prepared by extraction from human placenta by treatment by pepsin and refinement by salting out (Nishihara T. and Miyata T., Collagenous protein Symposium 3, 66–93, 1962).

The extracted and refined collagenous protein (final concentration of 1 mg/ml) was held in a pH 7.4 phosphate buffer at 37° C. to cause the formation of collagenous protein fibers. The later mentioned various samples were made copresent with the collagenous protein and the mixtures were irradiated with UV rays of 7.0 J/cm$^2$ energy (Toshiba FL20S.BLB lamp, UVA region, peak 365 nm) (UV intensity: 1.4 mW/cm$^2$, irradiation time: 90 minutes).

The irradiated collagenous protein was analyzed by the electrophoresis method and a densitometer (fluorescent light densitometer F-808 made by Cosmo Co.) to measure the ratio of the collagenous protein crosslinked due to the above UV irradiation.

Next, the rate of suppression of crosslinking of collagenous protein due to addition of the various types of samples mentioned later was found by the following formula. Note that the control was a phosphate buffer.

Suppression rate $(\%) = 100 - \{(A-C)/(B-C) \times 100\}$

Wherein:
A: Degree of crosslinking of collagenous protein of samples
B: Degree of crosslinking of collagenous protein of control
C: Degree of crosslinking without UV irradiation (2) The test results when studying the synergistic effects on the action obstructing the formation of collagenous protein crosslinking in the case of joint use of one of the long wavelength UV (UVA) absorbers, that is, sodium 2-hydroxy-4-methoxybenzophenone-5-sulfonate, and the enzymolyzed solution obtained in Preparation Example 1 in accordance with the method of the above (1) are shown in Table II-1.

TABLE II-1

| Sample No. | Enzymolyzed solution obtained in Preparation Ex. 1 (wt %) | Sodium 2-hydroxy-4-methoxybenzo-phenone-5-sulfonate (wt %) | Suppression rate (%) |
|---|---|---|---|
| 1 | 5.0 | 30.0 | 80 |
| 2 | 5.0 | 20.0 | 85 |
| 3 | 5.0 | 10.0 | 81 |
| 4 | 5.0 | 5.0 | 75 |
| 5 | 5.0 | 1.0 | 68 |
| 6 | 5.0 | 0.5 | 62 |
| 7 | 5.0 | 0.1 | 55 |
| 8 | 5.0 | 0.05 | 47 |
| 9 | 5.0 | 0.01 | 42 |
| 10 | 5.0 | 0.005 | 40 |
| 11 | 5.0 | 0 | 40 |
| 12 | 0 | 0 | 0 |
| 13 | 0 | 0.5 | 11 |

From Table II-1, it is clear that in a test system where one of the long wavelength UV (UVA) absorbers, that is, sodium 2-hydroxy-4-methoxybenzophenone-5-sulfonate, and the enzymolyzed solution obtained in Preparation Example 1 are added together, a synergistic effect in obstructing formation of collagenous protein crosslinking is clearly obtained. That is, blending in the enzymolyzed solution obtained in Preparation Example 1 and the sodium 2-hydroxy-4-methoxybenzophenone-5-sulfonate together as effective ingredients is clearly an extremely useful formulation.

Test Example II-2 (Action Promoting Synthesis of Collagenous protein)

Eagle minimum essential medium (hereinafter referred to as "MEM") containing 5% by volume fetal calf serum (hereinafter referred to as "FCS") was used as the basic medium and human dermis-derived fibroblasts were used the cells.

The cells were cultured in the basic medium for a predetermined period, then (a) a medium including 5% by volume of the above enzymolyzed solution or (b) a medium including 5% by volume of the above enzymolzed solution and 0.1% by weight of 4-methoxy-4'tert-butyldibenzoylmethane was used for culturing at 37° C. for 5 days. During that time, the medium was replaced once. Further, the result of culturing using only the basic medium was used as a (c) blank.

The amount of collagenous protein and the amount of non-collagenous protein per $10^4$ cells were measured for the fibroblasts cultured by the above procedure to evaluate the effect of the present invention. Note that the amounts of the collagenous protein and the non-collagenous protein proteins were determined according to a method of WLADI MIRO JIMENEZ ET AL (HEPATOLOGY, 5(5), p815–818, 1985) using Fast Green FCF dye and Sirius Red F3B dye. The results are shown in FIG. 4.

As clear from the results shown in FIG. 4, the enzymolyzed solution obtained in Preparation Example 1 significantly promotes the synthesis of collagenous protein depending upon the concentration. On the other hand, when compared with the enzymolyzed solution obtained in Comparative Preparation Example 1, it was observed that the superior promotion of the synthesis of collagenous protein can be effected at a lower concentration. Thus, it was suggested that the present invention is extremely effective.

Test Example II-3 (Action Restoring UV Damage)

An Eagle MEM containing 10 percent by volume of FCS was used as the basic medium and human dermis-derived fibroblasts were used as the cells.

The cells were cultured in the basic medium for a predetermined period, then (a) a medium including 10% by volume of the above enzymolyzed solution, (b) a medium containing 0.1% by weight of 2-hydroxy-4-methoxybenzophenone, or (c) a medium including 10% by volume of the above enzymolzed solution and 0.1% by weight of 2-hydroxy-4-methoxybenzophenone was added and the result cultured at 37° C. for 10 days while irradiating UV rays by a UV lamp (FL20S.BLB lamp, made by Toshiba Corporation, 20 W). During that time, the medium was replaced twice. Further, the result of culturing using only the basic medium was used as a (d) blank.

The fibroblasts cultured by the above procedure were measured as to the cell count by isolating the cells using trypsin EDTA after culturing so as to investigate the action in restoring damage caused by UV rays. The results are shown in FIG. 5.

As clear from the results shown in FIG. 5, either of the enzymolyzed solution obtained in Preparation Example 1 and 2-hydroxy-4-methoxybenzophenone alone exhibits a clear action restoring cells from damage caused by UV rays. Further, when these two are combined, the action restoring cells from UV damage rises synergistically. That is, by blending as effective ingredients the enzymolyzed solution and the 2-hydroxy-4-methoxybenzophenone together, the activity of the fibroblasts can be expected to be maintained high as it is even after exposure to UV rays. Accordingly, the blending of the enzymolyzed solution and the 2-hydroxy-4-methoxybenzophenone together as effective ingredients is clearly an extremely useful formulation.

Below, various types of formulation of the anti-aging cosmetic composition according to the present invention will be explained as examples.

Example II-1. (Cosmetic Lotion)

| | | |
|---|---|---|
| (1) | Enzymolyzed solution obtained in Preparation Example 1 | 10.0 wt% |
| (2) | Sodium hydroxy-4-methoxybenzophenone 5-sulfonate | 0.1 |
| (3) | Tocopherol acetate | 0.01 |
| (4) | Glycerol | 4.0 |
| (5) | 1,3-butylene glycol | 4.0 |
| (6) | Ethanol | 8.0 |
| (7) | Polyoxyethylene (60) hardened castor oil | 0.5 |
| (8) | Methylparaben | 0.2 |
| (9) | Citric acid | 0.05 |
| (10) | Sodium citrate | 0.1 |
| (11) | Perfume | 0.05 |
| (12) | Purified water | Balance |

Preparation Method

The enzymolyzed solution obtained in Preparation Example 1 (1), sodium hydroxy-4-methoxybenzophenone-5-sulfonate (2), citric acid (9), sodium citrate (10), glycerol (4), and 1,3-butylene glycol (5) were dissolved in purified water (12). Separately, the polyethylene (60) hardened castor oil ((7), tocopherol acetate (3), perfume (11), and methylparaben (8) were dissolved in ethanol. To this was added the above solution of purified water to dissolve the same. The result was filtered to obtain the desired cosmetic water.

Example II-2. (Cream)

| | | |
|---|---|---|
| (1) | Cetostearyl alcohol | 3.5 wt% |
| (2) | Squalane | 40.0 |
| (3) | Beeswax | 3.0 |
| (4) | Hydrogenated lanolin | 5.0 |
| (5) | Ethyl paraben | 0.3 |
| (6) | Polyoxyethylene (20) sorbitan monopalmitate ester | 2.0 |
| (7) | Monoglyceride stearate | 2.0 |
| (8) | Sodium N-stearoylglutamate | 0.5 |
| (9) | 4-methoxy-4'-tert-butyldibenzoylmethane | 1.0 |
| (10) | Octyl methoxycinnamate | 10.0 |
| (11) | Retinol acetate | 2.0 |
| (12) | Primrose oil | 0.05 |
| (13) | Perfume | 0.03 |
| (14) | Enzymolyzed solution obtained in Preparation Example 1 | 5.0 |
| (15) | 2-aminoethylsulfinic acid | 0.1 |
| (16) | 1,3-butylene glycol | 5.0 |
| (17) | Polyethylene glycol 1500 | 5.0 |
| (18) | Purified water | Balance |

Preparation Method

The cetostearyl alcohol (1), squalane (2), beeswax (3), hydrogenated lanolin (4), ethylparaben (5), polyoxyethylene (20) sorbitan monopalmitate ester (6), monoglyceride stearate (7), sodium N-stearoylglutamate (8), 4-methoxy-4'-tert-butyldibenzoylmethane (9), octyl methoxycinnamate (10), retinol acetate (11), primrose oil (12), and perfume (13) were heated to melt (oil phase). The enzymolyzed solution obtained in Preparation Example 1 (14), the 2-aminoethylsulfinic acid (15), 1,3-butylene glycol (16), and polyethylene glycol 1500 (17) were dissolved in purified water (17) and held at 70° C. (aqueous phase). The oil phase was added to the aqueous phase while stirring. Next, the mixture was processed by a homomixer to pulverize the emulsion particles, then the result was quickly cooled while stirring to obtain the desired cream.

Example II-3. (Emulsion)

| (1) 2-ethylhexyl paradimethylaminobenzoate | 0.1 wt% |
|---|---|
| (2) Mono-2-ethylhexyl diparamethoxycinnamate | 0.2 |
| (3) Stearic acid | 1.5 |
| (4) Cetyl alcohol | 0.5 |
| (5) Beeswax | 2.0 |
| (6) Polyoxyethylene (10) monooleate ester | 2.0 |
| (7) L-arginine | 0.3 |
| (8) Sodium L-glutamate | 0.02 |
| (9) PCA-Na | 0.05 |
| (10) Enzymolyzed solution obtained in Preparation Example 1 | 1.0 |
| (11) Tranexamic acid | 1.0 |
| (12) Propylene glycol | 5.0 |
| (13) Glycerol | 3.0 |
| (14) Ethanol | 3.0 |
| (15) Ethylparaben | 0.3 |
| (16) Perfume | 0.03 |
| (17) Carboxyvinyl polymer | 0.12 |
| (18) Purified water | Balance |

Preparation Method

The enzymolyzed solution obtained in Preparation Example 1 (10), tranexamic acid (11), L-arginine (7), sodium L-glutamate (8), PCA-Na (9), propylene glycol (12), glycerol (13), ethanol (14), and carboxyvinyl polymer (17) were added to purified water (18) and heated to dissolve and held at 70° C. (aqueous phase). Next, the other components were mixed and the result was heated to dissolve and held at 70° C. (oil phase). The oil phase was added to the aqueous phase and preliminarily emulsified, then was homogeneously emulsified by a homomixer. Next, the result was rapidly cooled with stirring to obtain the desired emulsion.

Example II-4. (Foam Mask)

| (1) Enzymolyzed solution obtained in Preparation Example 1 | 0.1 wt% |
|---|---|
| (2) 2-hydroxy-4-methoxybenzophenone | 0.1 |
| (3) Stearic acid | 1.0 |
| (4) Behenic acid | 1.0 |
| (5) Self emulsifying glycerin monostearate | 1.5 |
| (6) Polyoxyethylene (5) glycerol monostearate | 2.5 |
| (7) Batyl alcohol | 1.5 |
| (8) Perfume | 0.05 |
| (9) Glycerol | 5.0 |
| (10) 1,3-butylene glycol | 5.0 |
| (11) Polyethylene glycol 1500 | 3.0 |
| (12) Methylparaben | 0.1 |
| (13) Potassium hydroxide | 0.15 |
| (14) Purified water | Balance |
| (15) Liquified petroleum gas | 6.0 |
| (16) Dimethyl ether | 2.0 |

Preparation Method

The enzymolyzed solution obtained in Preparation Example 1 (1), glycerol (9), 1,3-butylene glycol (10), polyethylene glycol 1500 (11), methylparaben (12), and potassium hydroxide (13) were added to purified water (14) and heated and dissolved at 70° C. (aqueous phase). Next, the other components were mixed and heated to melt, then were held at 70° C. (oil phase). The oil phase was added to the aqueous phase and the two were homogeneously mixed and then cooled. This homogeneous mixture was then packed in containers. Finally, liquified gas and dimethyl ether were added as propellants to obtain the desired foam mask.

Example II-5. (Ointment)

| (1) Enzymolyzed solution obtained in Preparation Example 1 | 1.1 wt% |
|---|---|
| (2) Sodium 2-hydroxy-4-methoxybenzophenone 5-sulfonate | 0.5 |
| (3) Octyl paradimethylaminobenzoate | 4.0 |
| (4) Butylmethoxybenzoylmethane | 1.0 |
| (5) Tocopherol acetate | 0.5 |
| (6) Retinol palmitate | 1.0 |
| (7) Stearyl alcohol | 18.0 |
| (8) Japanese wax | 20.0 |
| (9) Polyoxyethylene (19) monooleate ester | 0.25 |
| (10) Glycerin monostearate ester | 0.3 |
| (11) Vaseline | 32.0 |
| (12) Purified water | Balance |

Preparation Method

The enzymolyzed solution obtained in Preparation Example 1 (1) and the sodium 2-hydroxy-4-methoxybenzophenone-5-sulfonate (2) were dissolved in purified water (12) and the result was held at 70° C. (aqueous phase). The other components were mixed and melted at 70° C. (oil phase). The oil phase was added to the aqueous phase and the result was homogeneously emulsified by a homomixer, then was cooled to obtain the desired ointment.

Example II-6. (Sunblocking Emulsion)

| (1) Stearic acid | 2.0 wt% |
|---|---|
| (2) Cetyl alcohol | 0.5 |
| (3) Liquid paraffin | 10.0 |
| (4) Polyoxyethylene (10) oleate ester | 1.0 |
| (5) Sorbitan trioleate | 1.0 |
| (6) 2-hydroxy-4-methoxybenzophenone | 3.0 |
| (7) 2,2'-hydroxy-5-methylphenylbenzotriazole | 1.0 |
| (8) Glycerylmono-2-ethylhexanoyl-diparamethoxycinnamate | 1.0 |
| (9) octyl methoxycinnamate | 7.0 |
| (10) Ethylparaben | 0.3 |
| (11) Perfume | 0.2 |
| (12) 1,3-butylene glycol | 5.0 |
| (13) Dipropylene glycol | 3.0 |
| (14) Enzymolyzed solution obtained in preparation Example 1 | 5.0 |
| (15) Arbutin | 3.0 |
| (16) Carboxyvinyl polymer | 0.15 |
| (17) Trisodium edetate | 0.05 |
| (18) Triethanol amine | 0.4 |
| (19) Silica | 2.0 |
| (20) Talc | 2.0 |
| (21) Titanium oxide | 3.0 |
| (22) Zinc oxide | 3.0 |
| (23) Purified water | Balance |

Preparation Method

The components of the 1,3-butylene glycol (12) to the triethanol amine (18) were added to purified water (23) to dissolve, then the silica (19) to zinc oxide (22) were dispersed and the result held at 70° C. On the other hand, the stearic acid (1) to perfume (11) were heated, mixed, and melted, then added to the aqueous phase. After the addition, the mixture was homogeneously emulsified by a homomixer, then was rapidly cooled while stirring to obtain the desired sunblocking emulsion.

Example II-7. (Sunblocking Cream)

| | | |
|---|---|---|
| (1) | Decamethylcyclopentasiloxane | 30.0wt% |
| (2) | Liquid paraffin | 5.0 |
| (3) | Polyoxyalkylene modified organopolysiloxane | 1.5 |
| (4) | Distearyldimethyl ammonium chloride | 0.6 |
| (5) | Octyl methoxycinnamate | 12.0 |
| (6) | 4-tert-butyl-4'-ethoxydibenzoylmethane | 0.1 |
| (7) | Glycerylmono-2-ethylhexanoyl diparamethoxy-cinnamate | 0.1 |
| (8) | Ethylparaben | 0.2 |
| (9) | Perfume | 0.3 |
| (10) | Titanium oxide | 10.0 |
| (11) | Zinc oxide | 5.0 |
| (12) | Talc | 2.0 |
| (13) | Glycerol | 5.0 |
| (14) | Enzymolyzed solution obtained in Preparation Example 1 | 0.6 |
| (15) | Smecton | 1.0 |
| (16) | Purified water | Balance |

Preparation Method

The decamethylcyclopentasiloxane (1) to perfume (9) were heated, mixed, and melted at 70° C. (oil phase). Next, the titanium oxide (10) to the enzymolyzed solution obtained in Preparation Example 1 (14) were added to the oil phase. This was dispersed and mixed by a disperser. On the other hand, the glycerin (13) to smecton (15) were mixed, melted, and dispersed in refined water (16) and held at 70° C. (aqueous phase). This was added gradually to the oil phase while stirring by a disperser. This was sufficiently homogeneously stirred, then cooled to obtain the desired sunblocking cream.

Example II-8. (Sunblocking Cream)

| | | | |
|---|---|---|---|
| (1) | Decamethylcyclopentasiloxane | 30.0 | wt% |
| (2) | Liquid paraffin | 5.0 | |
| (3) | Polyoxyalkylene modified organopolysiloxane | 1.5 | |
| (4) | Distearyldimethyl ammonium chloride | 0.6 | |
| (5) | Octyl methoxycinnamate | 12.0 | |
| (6) | 4-tert-butyl-4'-ethoxydibenzoylmethane | 0.1 | |
| (7) | Glycerylmono-2-ethylhexanoyl-diparamethoxy-cinnamate | 0.1 | |
| (8) | Ethylparaben | 0.2 | |
| (9) | Perfume | 0.3 | |
| (10) | Titanium oxide | 10.0 | |
| (11) | Zinc oxide | 5.0 | |
| (12) | Talc | 2.0 | |
| (13) | Glycerol | 5.0 | |
| (14) | Enzymolyzed solution obtained in Preparation Example 1 | 0.006 | |
| (15) | Smecton | 1.0 | |
| (16) | Purified water | Balance | |

Preparation Method

The decamethylcyclopentasiloxane (1) to perfume (9) were heated, mixed, and melted at 70° C. (oil phase). Next, the titanium oxide (10) to the enzymolyzed solution obtained in Preparation Example 1 (14) were added to the oil phase. This was dispersed and mixed by a disperser. On the other hand, the glycerol (13) to smecton (15) were mixed, melted, and dispersed in purified water (16) and held at 70° C. (aqueous phase). This was added gradually to the oil phase while stirring by a disperser. This was sufficiently homogeneously stirred, then cooled to obtain the desired sunblocking cream.

Example II-9. (Hair Tonic)

| | | |
|---|---|---|
| (1) | Hinokitiol | 0.1 wt% |
| (2) | Swertia extract | 1.0 |
| (3) | Vitamin $B_6$ | 0.2 |
| (4) | Vitamin E | 0.01 |
| (5) | Propylene glycol | 2.0 |
| (6) | 4-methoxy-4'-tert-butyldibenzoylmethane | 5.0 |
| (7) | Enzymolyzed solution obtained in Preparation Example 1 | 10.0 |
| (8) | Ethyl alcohol | 60.0 |
| (9) | Surfactant | 0.1 |
| (10) | Purified water | Balance |

Preparation Method (1) to (6) and (9) were dissolved in (8) ethyl alcohol (alcohol phase). The enzymolyzed solution obtained in Preparation Example 1 (7) was added to purified water (10) (aqueous phase). The aqueous phase was added to the previously prepared alcohol phase to dissolve it, then the mixture was made homogeneous and then filtered.

Example II-10 and Comparative Example II-1

The cosmetic composition prepared by replacing (6) in the formulation of Example II-6 with water was used as Example II-10 and the cosmetic composition prepared by replacing the "enzymolyzed solution obtained in Preparation Example 1" in Example II-10 with water was used as Comparative Example II-1.

The cosmetic composition obtained in Examples II-6 and II-10 and Comparative Example II-1 were subjected to a monitor test as shown below. The results are shown in Table II-2.

Monitor test

One hundred healthy adult women of age 25 to 57 extracted at random were used as test subjects. The cosmetic compositions were used on the skin of the face every day for one month, then a study was made of effect of improvement on the large wrinkles and small wrinkles.

(a) Effect of improvement on large wrinkles and small wrinkles

The state of the skin was observed visually and evaluated based on the following evaluation criteria.

Evaluation Criteria

A: Completely disappeared

B: Somewhat reduced

C: No change

D: Slightly increased

E: Increased (b) Effect on stiffness and sagging of skin

The state of the skin was observed visually and evaluated based on the following evaluation criteria.

Evaluation Criteria

A: Extremely improved

B: Improved

C: No change

D: Became somewhat noticeable

E: Became noticeable

Note that in the monitor test, when using the cosmetics obtained in Examples II-6 and II-8 and Comparative Example II-1, not even one test subject experienced an abnormality of the skin.

TABLE II-2

| | Effect on large wrinkles and small wrinkles (persons) | | | | | Effect on stiffness and sagging (persons) | | | | |
|---|---|---|---|---|---|---|---|---|---|---|
| | A | B | C | D | E | A | B | C | D | E |
| Ex. II-6 | 83 | 14 | 3 | 0 | 0 | 79 | 15 | 6 | 0 | 0 |
| Ex. II-10 | 78 | 15 | 6 | 1 | 0 | 75 | 19 | 2 | 2 | 2 |
| Comp. Ex. II-1 | 24 | 30 | 27 | 18 | 1 | 6 | 19 | 53 | 21 | 1 |

Test Example II-4

The amounts of collagenous protein and non-collagenous protein per $10^4$ cells cultured in a sample containing the enzymolyzed solution obtained in Preparation Example 1 and 2.5% or 5% of Fine Rice Silky or 5% of Oryze Noble (i.e., the alkali extract of hypoallergenic rice according to the present invention).

The results are shown in Table II-3 below and FIGS. 6 and 7.

TABLE II-3

| Sample | Collagenous protein (ABS) | ±SD | Test | Non-Collagenous protein (ABS) | ±SD | Test | Non Collagenous protein % |
|---|---|---|---|---|---|---|---|
| Blank | 0.047 | 0.009 | — | 0.024 | 0.003 | — | 100 |
| Fine Rice Silky 2.5% | 0.069 | 0.003 | ** | 0.035 | 0.003 | ** | 146 |
| Fine Rice Silky 5% | 0.077 | 0.003 | ** | 0.039 | 0.003 | ** | 163 |
| Oryze Noble 5% | 0.061 | 0.004 | ** | 0.030 | 0.002 | ** | 125 |

*Significant with 5% level
*Significant with 1% level

As clear from the results shown in Table II-3, in the case of use of the cosmetic obtained in Example II-10, an improvement was observed from the viewpoint of the large wrinkles and small wrinkles and stiffness and sagging of the skin compared with the case of use of the cosmetic obtained in Comparative Example II-1. Further, in the case of use of the cosmetic obtained in Example II-6, it was learned there was an improvement in the large wrinkles and small wrinkles and the stiffness and sagging of the skin compared with the case of use of the cosmetic obtained in Example II-10. This shows that blending of the enzymolyzed solution obtained in Preparation Example 1 and 2-hydroxy-4-methoxybenzophenone together as effective ingredients is extremely effective as a formulation.

As explaining above according to the present invention, by including as effective ingredients an enzymolyzed solution obtained by treating an alkali extract of hypoallergenic rice with one or more types of enzymes and also one or more types of UV protective agents, it is possible to provide an anti-aging cosmetic exhibiting an anti-aging effect superior even to an anti-aging cosmetic in which the above enzymolyzed solution is blended alone as an effective ingredient. That is, it is possible to provide a cosmetic exhibiting the superior cosmetic effect of being able to maintain skin with elasticity and free from wrinkles or sagging and of preventing aging of the skin and maintaining a young state of the skin by suppressing the damage to the skin aggravated by exposure to UV rays, such as the reduction in the activity of the fibroblasts and the crosslinking of collagenous protein, and further by restoring the damage received.

We claim:

1. An anti-aging cosmetic composition comprising a solution obtained by treating, with at least one enzyme, an alkali extract of a hypoallergenic rice obtained by treating rice with a proteinase;

wherein said at least one enzyme is selected from the group consisting of an actinase, a pepsin, a trypsin, a papain, a peptidase, and bromelin and wherein said at least one enzyme is used in an amount of not tore than 0.05 parts by weight of the alkali extract.

2. An anti-aging cosmetic composition as claimed in claim 1, wherein the enzyme for treating the alkali extract is a combination of:

(A) Actinase and (B) at least one proteinase selected from the group consisting of pepsin, trypsin, papain, peptidase, and bromelin.

3. An anti-aging cosmetic composition of claim 1 further comprising at least one UV protective agent.

4. An anti-aging cosmetic composition as claimed in claim 3, wherein the enzyme for treating the alkali extract is a combination of:

(A) Actinase and (B) at least one proteinase selected from the group consisting of pepsin, trypsin, papain, peptidase, and bromelin.

5. An anti-aging cosmetic composition as claimed in claim 3, wherein said UV protective agent includes at least one long wavelength UV protective agent.

6. An anti-aging cosmetic composition as claimed in claim 5, wherein said long wavelength UV protecting agent is 4-methoxy-4'tert-'butyldibenzoylmethane or a benzophenone UW absorber.

7. An anti-aging cosmetic composition as claimed in claim 3, wherein the solution obtained by enzymatic treatment of the alkali extract is contained in a range of 0.00001 to 10.0% by weight of the anti-aging cosmetic composition as a whole.

8. An anti-aging cosmetic composition as claimed in claim 7, wherein the solution obtained by enzymatic treatment of the alkali extract is contained in a range of 0.0001 to 2.0% by weight of the anti-aging cosmetic composition as a whole.

9. An anti-aging cosmetic composition as claimed claims 3, wherein the UV protective agents are contained in a range of 0.01 to 30.0% by weight of the anti-aging cosmetic composition as a whole.

10. An anti-aging cosmetic composition as claimed in claim 9, wherein the UV protective agent is contained in a range of 0.1 to 20.0% by weight of the entire anti-aging cosmetic composition.

11. An anti-aging cosmetic composition as claimed in claim 4, wherein the solution obtained by enzymatic treatment of the alkali extract is contained in a range of 0.00001 to 10.0% by weight of the anti-aging cosmetic composition as a whole.

12. An anti-aging cosmetic composition as claimed in claim 5, wherein the solution obtained by enzymatic treatment of the alkali extract is contained in a range of 0.00001 to 10.0% by weight of the anti-aging cosmetic composition as a whole.

13. An anti-aging cosmetic composition as claimed in claim 6, wherein the solution obtained by enzymatic treatment of the alkali extract is contained in a range of 0.00001 to 10.0% by weight of the anti-aging cosmetic composition as a whole.

14. An anti-aging cosmetic composition as claimed in claim 4, wherein the UV protective agents are contained in a range of 0.01 to 30.0% by weight of the entire anti-aging cosmetic composition.

15. An anti-aging cosmetic composition as claimed in claim 5, wherein the UV protective agents are contained in a range of 0.01 to 30.0% by weight of the entire anti-aging cosmetic composition.

16. An anti-aging cosmetic composition as claimed in claim 6, wherein the UV protective agents are contained in a range of 0.01 to 30.0% by weight of the entire anti-aging cosmetic composition.

17. An anti-aging cosmetic composition as claimed in claim 7, wherein the UV protective agents are contained in a range of 0.01 to 30.0% by weight of the entire anti-aging cosmetic composition.

18. An anti-aging cosmetic composition as claimed in claim 8, wherein the UV protective agents are contained in a range of 0.01 to 30.0% by weight of the entire anti-aging cosmetic composition.

19. An anti-aging cosmetic composition as claimed in claim 1, wherein the hypoallergenic rice has 50–70% by weight of globulin removed.

* * * * *

UNITED STATES PATENT AND TRADEMARK OFFICE
CERTIFICATE OF CORRECTION

PATENT NO. : 5,853,705
DATED : December 29, 1998
INVENTOR(S) : Yasukazu NAKAYAMA et al.

It is certified that error appears in the above-indentified patent and that said Letters Patent is hereby corrected as shown below:

On the title page,
item [73] Assignee:, kindly insert --TECHNOBLE CO., LTD., Osaka-shi, Japan--.

Signed and Sealed this

Twenty-sixth Day of October, 1999

Attest:

Q. TODD DICKINSON

*Attesting Officer*                    Acting Commissioner of Patents and Trademarks